United States Patent
Houser et al.

(10) Patent No.: US 10,143,513 B2
(45) Date of Patent: Dec. 4, 2018

(54) GEAR DRIVEN COUPLING BETWEEN ULTRASONIC TRANSDUCER AND WAVEGUIDE IN SURGICAL INSTRUMENT

(75) Inventors: Kevin L. Houser, Springboro, OH (US); Matthew C. Miller, Cincinnati, OH (US); Cory G. Kimball, Cincinnati, OH (US); John W. Willis, Cincinnati, OH (US); Timothy G. Dietz, Terrace Park, OH (US); Foster B. Stulen, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 1191 days.

(21) Appl. No.: 13/274,507

(22) Filed: Oct. 17, 2011

(65) Prior Publication Data

US 2012/0116263 A1   May 10, 2012

Related U.S. Application Data

(60) Provisional application No. 61/487,846, filed on May 19, 2011, provisional application No. 61/410,603, filed on Nov. 5, 2010.

(51) Int. Cl.
*A61B 18/14* (2006.01)
*H01M 2/26* (2006.01)
(Continued)

(52) U.S. Cl.
CPC .... *A61B 18/1442* (2013.01); *A61B 17/00234* (2013.01); *A61B 17/2812* (2013.01);
(Continued)

(58) Field of Classification Search
USPC .............................. 600/437, 446, 459; 601/2
See application file for complete search history.

(56) References Cited

U.S. PATENT DOCUMENTS

| | | |
|---|---|---|
| 1,754,806 A | 4/1930 | Stevenson |
| 3,297,192 A | 1/1967 | Swett |

(Continued)

FOREIGN PATENT DOCUMENTS

| | | |
|---|---|---|
| DE | 102008051866 | 10/2010 |
| DE | 102009013034 | 10/2010 |

(Continued)

OTHER PUBLICATIONS

U.S. Appl. No. 13/151,471, filed Jun. 2, 2011, Stulen.
(Continued)

*Primary Examiner* — Rochelle Turchen
(74) *Attorney, Agent, or Firm* — Frost Brown Todd LLC

(57) ABSTRACT

A surgical instrument is separable into a transducer unit and a lower body portion. The lower body portion includes a waveguide and a casing. The transducer unit includes a transducer and a geared mechanism operable to couple the transducer to the waveguide. In some versions the geared mechanism includes bevel gears coupled to a rack and pinion such that linear motion may be used to rotatably couple a transducer to a waveguide. The rack gear may further include a handle extending out of the transducer unit casing to be actuatable by a user. The rack gear may also be flexible or rigid. In other versions, the bevel gears may be coupled to a threaded shaft that is operable to translate the transducer into the waveguide to form an interference fit. The transducer unit may also include a slide lock mechanism to couple to the casing of the lower body portion.

17 Claims, 12 Drawing Sheets

(51) Int. Cl.

| | | |
|---|---|---|
| *H01M 2/10* | (2006.01) | |
| *A61B 18/12* | (2006.01) | |
| *A61B 17/00* | (2006.01) | |
| *A61B 17/32* | (2006.01) | |
| *A61B 18/00* | (2006.01) | |
| *A61B 18/04* | (2006.01) | |
| *H02J 7/00* | (2006.01) | |
| *A61B 17/28* | (2006.01) | |
| *A61N 7/00* | (2006.01) | |
| *A61B 34/00* | (2016.01) | |
| *A61B 90/40* | (2016.01) | |
| *A61B 46/10* | (2016.01) | |
| *H01M 10/46* | (2006.01) | |
| *H02J 7/02* | (2016.01) | |
| *H01M 10/48* | (2006.01) | |
| *A61B 90/00* | (2016.01) | |
| *A61B 17/064* | (2006.01) | |
| *A61B 17/285* | (2006.01) | |
| *A61B 17/29* | (2006.01) | |

(52) U.S. Cl.
CPC .......... *A61B 17/320068* (2013.01); *A61B 17/320092* (2013.01); *A61B 18/00* (2013.01); *A61B 18/04* (2013.01); *A61B 18/12* (2013.01); *A61B 18/1206* (2013.01); *A61B 18/14* (2013.01); *A61B 18/1445* (2013.01); *A61B 34/25* (2016.02); *A61B 46/10* (2016.02); *A61B 90/08* (2016.02); *A61B 90/40* (2016.02); *A61N 7/00* (2013.01); *H01M 2/10* (2013.01); *H01M 2/1016* (2013.01); *H01M 2/26* (2013.01); *H01M 10/46* (2013.01); *H01M 10/48* (2013.01); *H02J 7/0044* (2013.01); *H02J 7/0045* (2013.01); *H02J 7/0047* (2013.01); *H02J 7/025* (2013.01); *A61B 17/064* (2013.01); *A61B 17/285* (2013.01); *A61B 18/1233* (2013.01); *A61B 2017/0046* (2013.01); *A61B 2017/0084* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/0019* (2013.01); *A61B 2018/00178* (2013.01); *A61B 2018/00589* (2013.01); *A61B 2018/00595* (2013.01); *A61B 2018/00601* (2013.01); *A61B 2018/00607* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2090/0803* (2016.02); *A61B 2090/0813* (2016.02); *A61B 2090/0814* (2016.02); *H01M 2220/30* (2013.01); *H02J 2007/005* (2013.01); *Y10T 29/49005* (2015.01); *Y10T 29/49895* (2015.01); *Y10T 29/53913* (2015.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekumas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,871,493 A | 2/1999 | Sjostrom et al. |
| 5,873,873 A | 2/1999 | Smith et al. |
| 5,882,310 A | 3/1999 | Marian, Jr. |
| 5,893,835 A | 4/1999 | Witt et al. |
| 5,893,874 A | 4/1999 | Bourque et al. |
| 5,935,144 A | 8/1999 | Estabrook |
| 5,938,633 A | 8/1999 | Beupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | DiMatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |

(56) References Cited

U.S. PATENT DOCUMENTS

| | | |
|---|---|---|
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 | 3/2004 | Francischelli et al. |
| 6,717,193 B2 | 4/2004 | Olewine et al. |
| 6,730,042 B2 | 5/2004 | Fulton et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,846,155 B2 | 12/2010 | Houser et al. |
| 7,846,159 B2 | 12/2010 | Morrison et al. |
| 7,889,489 B2 | 2/2011 | Richardson et al. |
| 7,918,848 B2 | 4/2011 | Lau et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,608 B2 | 8/2012 | Omori et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 9,044,261 B2 | 6/2015 | Houser |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |

(56) References Cited

U.S. PATENT DOCUMENTS

| | | |
|---|---|---|
| 2005/0203546 A1 | 9/2005 | Van Wyk et al. |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0175964 A1* | 8/2007 | Shelton et al. ............ 227/180.1 |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0234708 A1* | 9/2008 | Houser et al. ................ 606/169 |
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0105750 A1* | 4/2009 | Price et al. ................... 606/206 |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1* | 6/2009 | Smith et al. .................. 606/169 |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0264940 A1 | 10/2009 | Beale et al. |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1* | 2/2010 | Prevost ............................ 606/80 |
| 2010/0060231 A1 | 3/2010 | Trainor et al. |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko |
| 2011/0074336 A1 | 3/2011 | Miller |
| 2011/0077514 A1 | 3/2011 | Ulric et al. |
| 2011/0080134 A1 | 4/2011 | Miller |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0221398 A1 | 9/2011 | Ferber |
| 2011/0224668 A1 | 9/2011 | Johnson et al. |
| 2011/0247952 A1 | 10/2011 | Habach et al. |
| 2011/0288573 A1 | 11/2011 | Yates et al. |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger et al. |
| 2013/0118733 A1 | 5/2013 | Kumar |
| 2013/0342962 A1 | 12/2013 | Fletcher et al. |
| 2014/0088739 A1 | 3/2014 | Ellis et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | 4602681 | 12/2010 |
| JP | 4836148 | 12/2011 |
| WO | WO 1997/024072 | 7/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |

(56) References Cited

FOREIGN PATENT DOCUMENTS

| WO | WO 2010/096174 | 8/2010 |
|---|---|---|
| WO | WO 2011/059785 | 5/2011 |
| WO | WO 2011/089270 | 7/2011 |

OTHER PUBLICATIONS

U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
International Search Report and Written Opinion dated Jul. 6, 2012 for PCT/US2011/059381.
Office Action Non-Final dated Aug. 6, 2013 for U.S. Appl. No. 13/151,471.
Restriction Requirement dated Jul. 5, 2013 for U.S. Appl. No. 13/151,488.
Office Action Non-Final dated Jun. 14, 2013 U.S. Appl. No. 13/151,498.
Restriction Requirement dated Jun. 24, 2013 U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805.
Office Action Non-Final dated Jun. 14, 2013 for U.S. Appl. No. 13/274,830.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
International Search Report dated Jan. 26, 2012 for Application No. PCT/US11/059220.
International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.

(56) References Cited

OTHER PUBLICATIONS

Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
U.S. Office Action, Notice of Allowance, dated Aug. 19, 2014 for U.S. Appl. No. 13/151,471.
U.S. Office Action, Non-Final, dated Aug. 14, 2014 for U.S. Appl. No. 13/151,481.
U.S. Office Action, Non-Final, dated Nov. 7, 2014 for U.S. Appl. No. 13/151,488.
U.S. Office Action, Notice of Allowance, dated Aug. 6, 2014 for U.S. Appl. No. 13/151,498.
U.S. Office Action, Non-Final, dated Nov. 6, 2014 for U.S. Appl. No. 13/151,503.
U.S. Office Action, Non-Final, dated Jul. 9, 2014 for U.S. Appl. No. 13/151,509.
U.S. Office Action, Notice of Allowance, dated Oct. 28, 2014 for U.S. Appl. No. 13/151,509.
U.S. Office Action, Notice of Allowance, dated Oct. 29, 2014 for U.S. Appl. No. 13/151,512.
U.S. Office Action, Restriction Requirement, dated Jul. 11, 2014 for U.S. Appl. No. 13/269,870.
U.S. Office Action, Non-Final, dated Jul. 29, 2014 for U.S. Appl. No. 13/270,667.
U.S. Office Action, Restriction Requirement, dated Jul. 9, 2014 for U.S. Appl. No. 13/270,684.
U.S. Office Action, Non-Final, dated Oct. 9, 2014 for U.S. Appl. No. 13/270,684.
U.S. Office Action, Restriction Requirement, dated Sep. 11, 2014 for U.S. Appl. No. 13/270,701.
U.S. Office Action, Restriction Requirement, dated Sep. 25, 2014 for U.S. Appl. No. 13/271,352.
U.S. Office Action, Restriction Requirement, dated Oct. 2, 2013 for U.S. Appl. No. 13/274,480.
U.S. Office Action, Final, dated Jul. 17, 2014 for U.S. Appl. No. 13/274,480.
U.S. Office Action, Final, dated Aug. 22, 2014 for U.S. Appl. No. 13/274,496.
U.S. Office Action, Non-Final, dated Oct. 8, 2014 for U.S. Appl. No. 13/274,516.
U.S. Office Action, Non-Final, dated Aug. 26, 2014 for U.S. Appl. No. 13/274,540.
U.S. Office Action, Non-Final, dated Aug. 14, 2014 for U.S. Appl. No. 13/274,805.
U.S. Office Action, Non-Final, dated Oct. 22, 2014 for U.S. Appl. No. 13/274,830.
U.S. Office Action, Non-Final, dated Sep. 9, 2014 for U.S. Appl. No. 13/275,514.
U.S. Office Action, Non-Final, dated Aug. 20, 2014 for U.S. Appl. No. 13/275,547.
U.S. Office Action, Non-Final, dated Oct. 23, 2014 for U.S. Appl. No. 13/275,563.
U.S. Office Action, Restriction Requirement, dated Jul. 9, 2014 for U.S. Appl. No. 13/276,660.
U.S. Office Action, Non-Final, dated Aug. 14, 2014 for U.S. Appl. No. 13/276,673.
U.S. Office Action, Notice of Allowance, dated Sep. 12, 2014 for U.S. Appl. No. 13/276,687.
U.S. Office Action, Non-Final, dated Aug. 20, 2014 for U.S. Appl. No. 13/276,725.
U.S. Office Action, Notice of Allowance, dated Oct. 7, 2014 for U.S. Appl. No. 13/276,745.
U.S. Office Action, Restriction Requirement, dated Sep. 24, 2014 for U.S. Appl. No. 13/277,328.
U.S. Appl. No. 13/151,471.
U.S. Appl. No. 13/151,481.
U.S. Appl. No. 13/151,498.
U.S. Appl. No. 13/151,509.
U.S. Appl. No. 13/151,512.
U.S. Appl. No. 13/270,667.
U.S. Appl. No. 13/270,684.
U.S. Appl. No. 13/274,540.
U.S. Appl. No. 13/274,805.
U.S. Appl. No. 13/276,687.
U.S. Appl. No. 13/276,725.

(56) References Cited

OTHER PUBLICATIONS

U.S. Appl. No. 13/276,745.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.
Restriction Requirement dated Jun. 11, 2014 for U.S. Appl. No. 13/151,512.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
Office Action Final dated Jun. 12, 2014 for U.S. Appl. No. 13/274,516.
Office Action Non-Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
U.S. Appl. No. 61/410,603, filed Nov. 5, 2010.
U.S. Appl. No. 61/487,846, filed May 19, 2011.
U.S. Appl. No. 13/151,488.
U.S. Appl. No. 13/151,503.
U.S. Appl. No. 13/269,870.
U.S. Appl. No. 13/269,684.
U.S. Appl. No. 13/270,701.
U.S. Appl. No. 13/271,352.
U.S. Appl. No. 13/271,364.
U.S. Appl. No. 13/274,480.
U.S. Appl. No. 13/274,496.
Australian First Examination Report dated Jun. 11, 2015 for Application No. AU2011323281.
Chinese First Office Action dated Apr. 16, 2015 for Application No. CN201180063919X.
Chinese First Office Action dated Jun. 1, 2015 for Application No. CN201180064098I.
Japanese Notification of Reasons for Refusal dated Aug. 25, 2015 for Application No. 2013-537831.
U.S. Office Action, Notice of Allowance, dated Nov. 21, 2014 for U.S. Appl. No. 13/151,471.
U.S. Office Action, Final, dated Apr. 1, 2015 for U.S. Appl. No. 13/151,481.
U.S. Office Action, Notice of Allowance, dated Nov. 21, 2014 for U.S. Appl. No. 13/151,498.
U.S. Office Action, Notice of Allowance, dated Feb. 25, 2015 for U.S. Appl. No. 13/151,509.
U.S. Office Action, Notice of Allowance, dated Feb. 17, 2015 for U.S. Appl. No. 13/151,512
U.S. Office Action, Non-Final, dated Jan. 5, 2015 for U.S. Appl. No. 13/269,870.
U.S. Office Action, Final, dated Aug. 14, 2015 for U.S. Appl. No. 13/269,870.
U.S. Office Action, Notice of Allowance, dated Dec. 17, 2014 for U.S. Appl. No. 13/270,667.
U.S. Office Action, Final, dated Mar. 17, 2015 for U.S. Appl. No. 13/270,684.
U.S. Office Action, Notice of Allowance, dated Jul. 28, 2015 for U.S. Appl. No. 13/270,684.
U.S. Office Action, Non-Final, dated Dec. 16, 2014 for U.S. Appl. No. 13/270,701.
U.S. Office Action, Non-Final, dated Mar. 26, 2015 for U.S. Appl. No. 13/271,352.
U.S. Office Action, Final, dated Jul. 15, 2015 for U.S. Appl. No. 13/271,352.
U.S. Office Action, Non-Final, dated Jul. 14, 2015 for U.S. Appl. No. 13/271,364.
U.S. Office Action, Non-Final, dated Apr. 2, 2015 for U.S. Appl. No. 13/274,496.
U.S. Office Action, Final, dated May 8, 2015 for U.S. Appl. No. 13/274,516.
U.S. Office Action, Notice of Allowance, dated Sep. 24, 2015 for U.S. Appl. No. 13/274,516.
U.S. Office Action, Notice of Allowance, dated Jan. 21, 2015 for U.S. Appl. No. 13/274,540.
U.S. Office Action, Notice of Allowance, dated Nov. 28, 2014 for Application No. 13/274,805.
U.S. Office Action, Notice of Allowance, dated Jan. 21, 2015 for U.S. Appl. No. 13/274,805.
U.S. Office Action, Notice of Allowance, dated Mar. 23, 2015 for U.S. Appl. No. 13/274,830.
U.S. Office Action, Non-Final, dated Feb. 25, 2015 for U.S. Appl. No. 13/275,495.
U.S. Office Action, Final, dated Mar. 10, 2015 for U.S. Appl. No. 13/275,547
U.S. Office Action, Final, dated Mar. 13, 2015 for U.S. Appl. No. 13/276,673.
U.S. Office Action, Notice of Allowance, dated Dec. 23, 2014 for U.S. Appl. No. 13/276,687.
U.S. Office Action, Non-Final, dated Jan. 29, 2015 for U.S. Appl. No. 13/276,707.
U.S. Office Action, Notice of Allowance, dated Mar. 13, 2015 for U.S. Appl. No. 13/276,725.
U.S. Office Action, Notice of Allowance, dated Dec. 19, 2014 for U.S. Appl. No. 13/276,745.
U.S. Office Action, Non-Final, dated Dec. 8, 2014 for U.S. Appl. No. 13/277,328.
U.S. Office Action, Final, dated Mar. 24, 2015 for U.S. Appl. No. 13/277,328.
U.S. Office Action, Notice of Allowance, dated Jun. 1, 2015 for U.S. Appl. No. 13/277,328.
U.S. Appl. No. 13/274,516.
U.S. Appl. No. 13/274,830.
U.S. Appl. No. 13/275,495.
U.S. Appl. No. 13/275,514.
U.S. Appl. No. 13/275,547.
U.S. Appl. No. 13/275,563.
U.S. Appl. No. 13/276,660.
U.S. Appl. No. 13/276,673.
U.S. Appl. No. 13/276,707.
U.S. Appl. No. 13/277,328.
U.S. Appl. No. 14/788,915.

\* cited by examiner

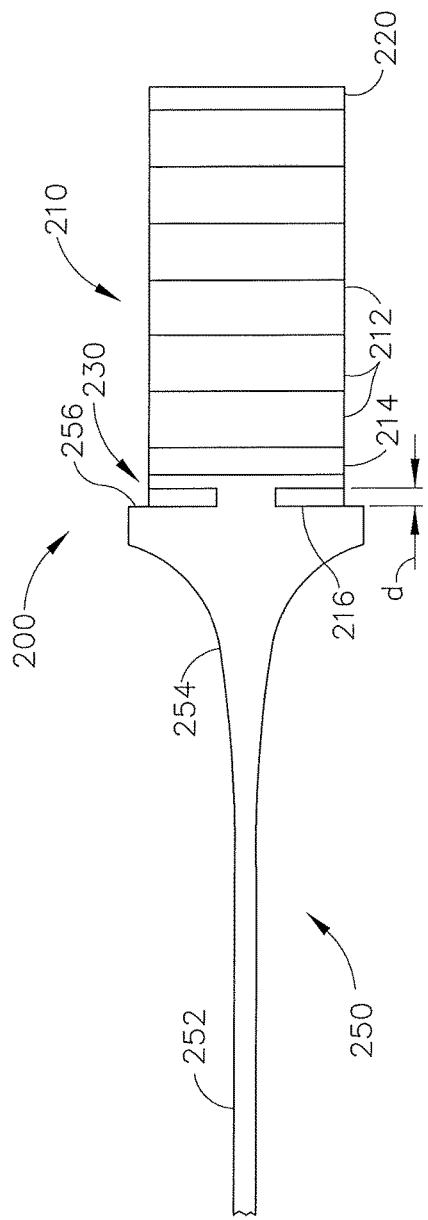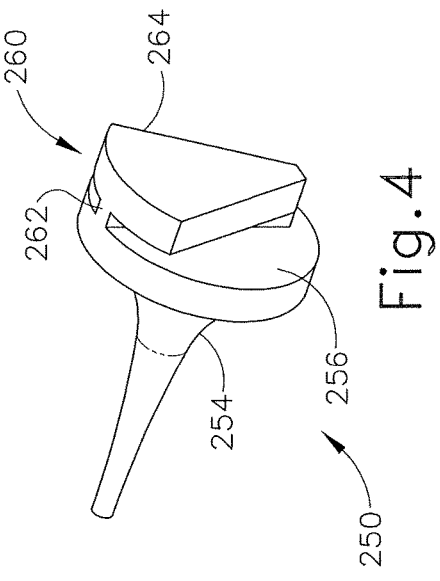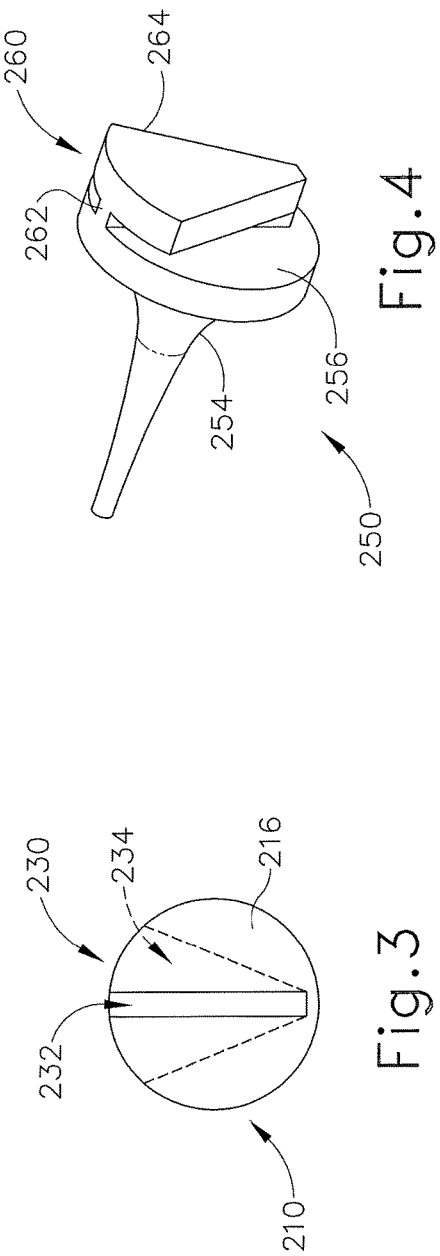

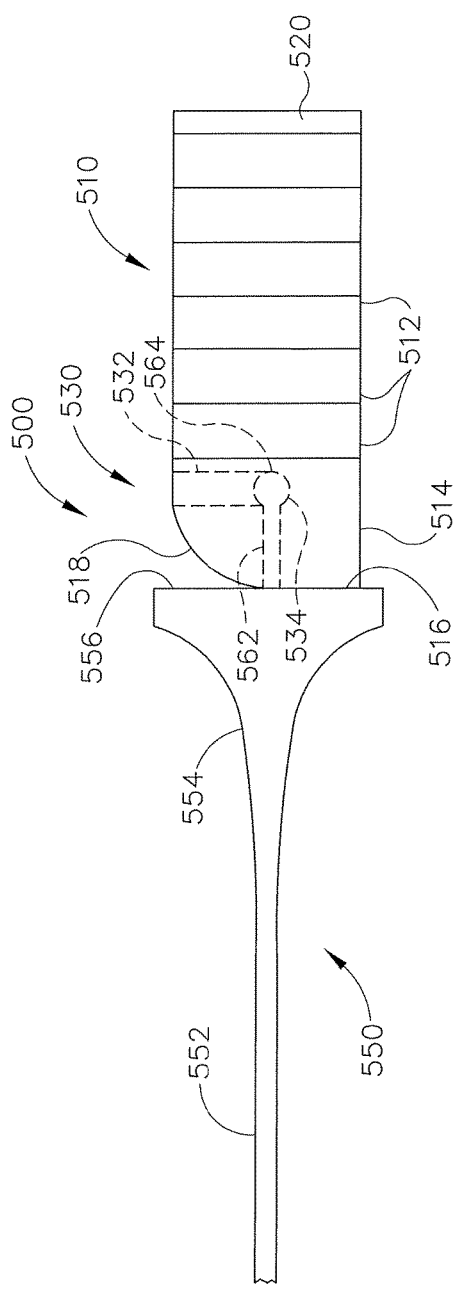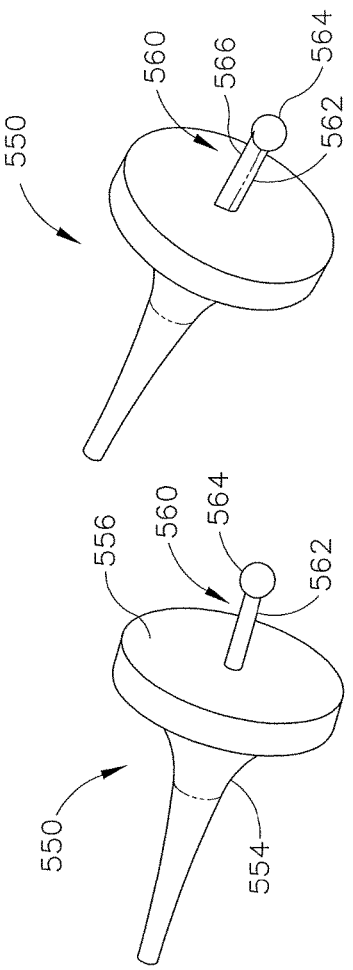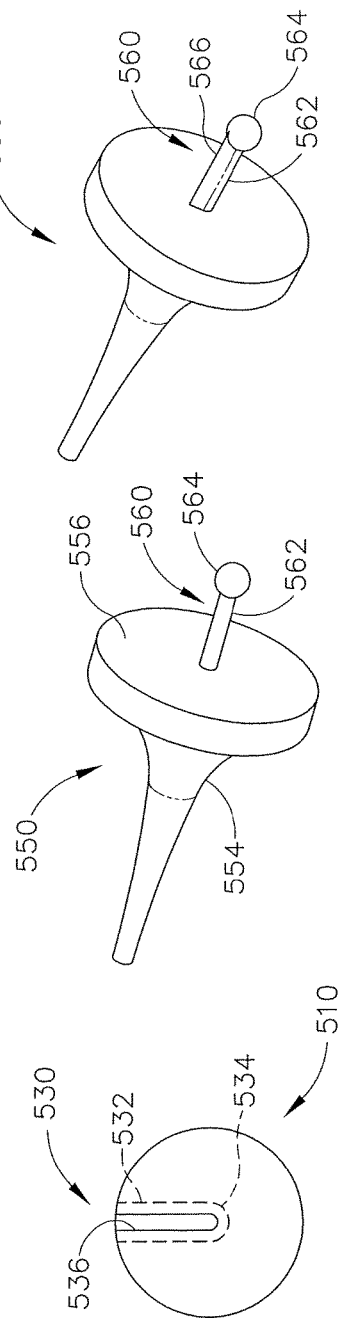

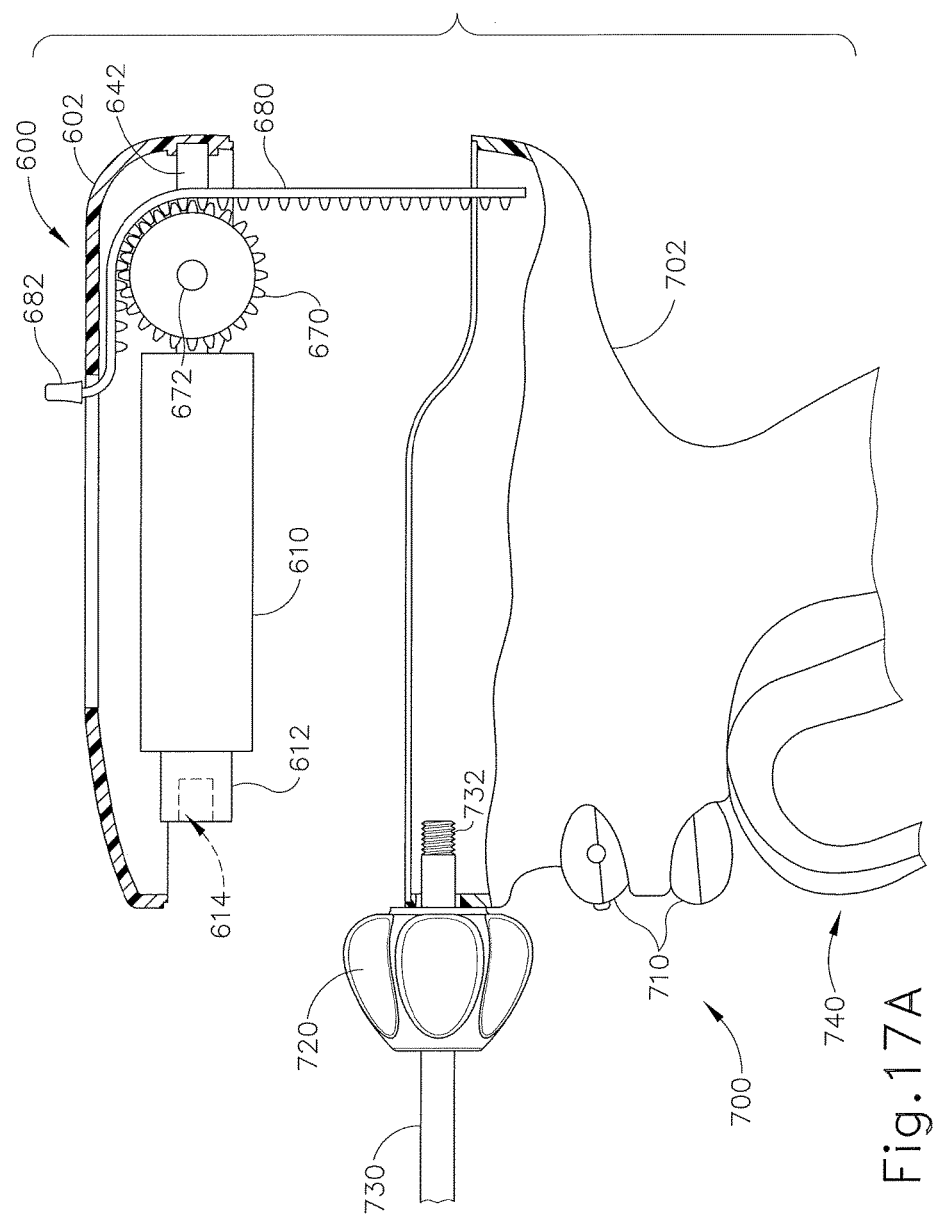

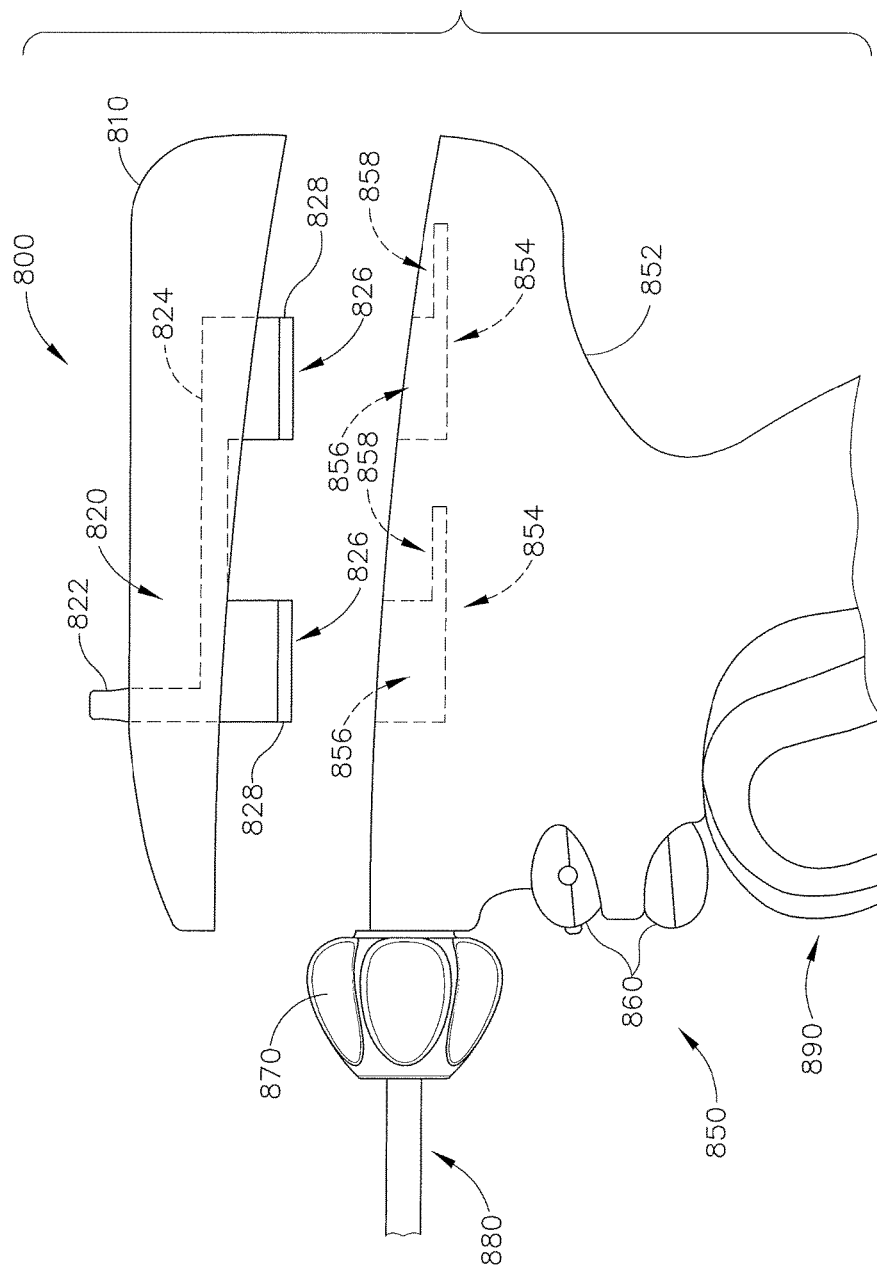

GEAR DRIVEN COUPLING BETWEEN ULTRASONIC TRANSDUCER AND WAVEGUIDE IN SURGICAL INSTRUMENT

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, now abandoned, entitled "Tissue Pad for Use with an Ultrasonic Surgical Instrument," published Apr. 13, 2006, the disclosure of which is incorporated by reference herein; U.S. Pat. Pub. No. 2007/0191713, now abandoned, entitled "Ultrasonic Device for Cutting and Coagulating," published Aug. 16, 2007, the disclosure of which is incorporated by reference herein; U.S. Pat. Pub. No. 2007/0282333, now abandoned, entitled "Ultrasonic Waveguide and Blade," published Dec. 6, 2007, the disclosure of which is incorporated by reference herein; U.S. Pat. Pub. No. 2008/0200940, now abandoned, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2 depicts a top plan view of an exemplary transducer assembly and waveguide assembly coupled together via a V-shaped slot interface;

FIG. 3 depicts a front elevation view of the transducer of FIG. 2 showing a V-shaped female slot;

FIG. 4 depicts a rear partial perspective view of the waveguide of FIG. 2 showing a V-shaped male connector;

FIG. 11 depicts a side elevation view of yet another exemplary transducer assembly and waveguide assembly coupled together via a ball joint interface;

FIG. 12 depicts a front elevation view of the transducer of FIG. 11 showing a ball shaft portion, a ball cup, and an arcuate slot portion;

FIG. 13 depicts a rear partial perspective view of the waveguide of FIG. 11 showing a ball connector;

FIG. 14 depicts a rear partial perspective view of an exemplary alternative waveguide assembly having an asymmetric shaft for use with the transducer of FIG. 12;

FIG. 17A depicts a side elevation view of an exemplary lower handle portion and the transducer unit of FIG. 16 showing the rack gear and pinion gear for coupling the transducer to an exemplary waveguide;

FIG. 18 depicts a side elevation view of an exemplary transducer unit having a slide lock assembly to couple the transducer unit to an exemplary lower handle portion.

Figure 1:
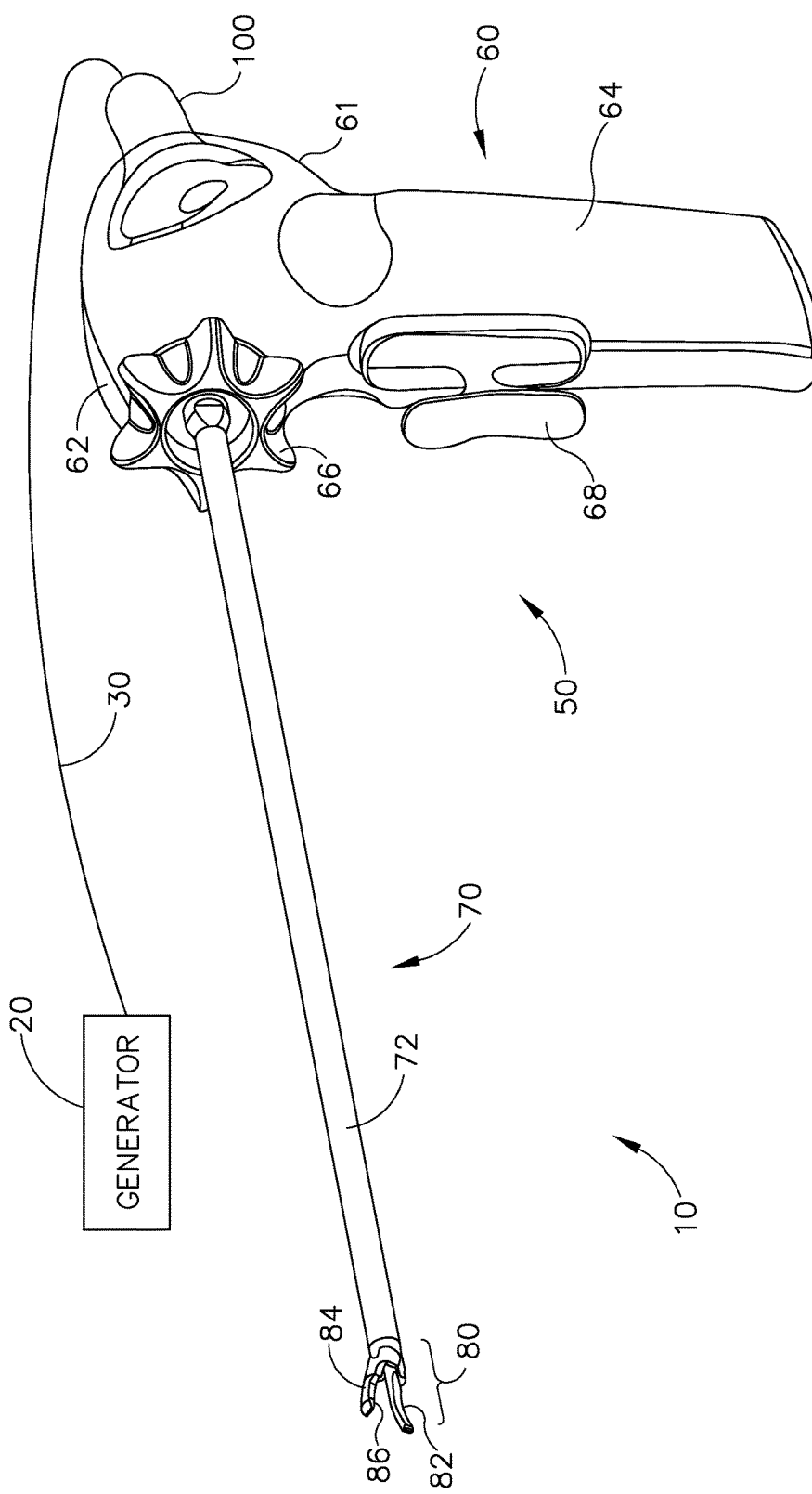
FIG. 1 depicts a perspective view of an exemplary surgical system having a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) coupling generator (20) to surgical instrument (50). In some versions, generator (20) comprises a GEN 300 sold by Ethicon Endo-Surgery, Inc. of Cincinnati, Ohio. By way of example only, generator (20) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. While surgical instrument (50) is described herein as an ultrasonic surgical instrument, it should be understood that the teachings herein may be readily applied to a variety of surgical instruments, including but not limited to endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein. For instance, surgical device (50) may include an integral and portable power source such as a battery, etc. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured as an elongated, thin tubular assembly for endoscopic use, but it should be understood that transmission assembly (70) may alternatively be a short assembly, such as those disclosed in U.S. Pat. Pub. No. 2007/0282333, now abandoned, entitled "Ultrasonic Waveguide and Blade," published Dec. 6, 2007, and U.S. Pat. Pub. No. 2008/0200940, now abandoned, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) that is mechanically and acoustically coupled to the waveguide, a clamp arm (84) operable to pivot at the proximal end of transmission assembly (70), and a clamp pad (86) coupled to clamp arm (84).

In some versions, transducer (100) comprises a plurality of piezoelectric elements (not shown) that are compressed between a first resonator (not shown) and a second resonator (not shown) to form a stack of piezoelectric elements. The piezoelectric elements may be fabricated from any suitable material, for example, lead zirconate-titanate, lead metaniobate, lead titanate, and/or any suitable piezoelectric crystal material, for example. Transducer (100) further comprises electrodes, including at least one positive electrode and at least one negative electrode, that are configured to create a voltage potential across the one or more piezoelectric elements, such that the piezoelectric elements convert the electrical power into ultrasonic vibrations. When transducer (100) of the present example is activated, transducer (100) is operable to create linear oscillations or vibrations at an ultrasonic frequency (such as 55.5 kHz). When transducer (100) is coupled to transmission assembly (70), these linear oscillations are transmitted through the internal waveguide of transmission assembly (70) to end effector (80). In the present example, with blade (82) being coupled to the waveguide, blade (82) thereby oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to cauterize the tissue. One merely exemplary suitable ultrasonic transducer (100) is Model No. HP054, sold by Ethicon Endo-Surgery, Inc. of Cincinnati, Ohio, though it should be understood that any other suitable transducer may be used. It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein.

Multi-piece handle assembly (60) of the present example comprises a mating housing portion (62) and a lower portion (64). Mating housing portion (62) defines a cavity within multi-piece handle assembly (60) and is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Lower portion (64) of multi-piece handle assembly (60) shown in FIG. 1 includes a trigger (68) and is configured to be grasped by a user using a single hand. One merely exemplary alternative version for lower portion (64) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. In some versions toggle buttons are located on a distal surface of lower portion (64) and are operable to selectively activate transducer (100) at different operational levels using generator (20). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Furthermore, any other number of toggle buttons may be provided.

While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). Such a trigger portion may be operable to activate transducer (100) and may be remote from mating housing portion (62). Multi-piece handle assembly (60) may be constructed from a durable plastic casing (61) (such as polycarbonate or a liquid crystal polymer), ceramics, metals and/or any other suitable material as will be apparent to one of ordinary skill in the art in view of the teachings herein. Other configurations for multi-piece handle assembly (60) will also be apparent to those of ordinary skill in the art in view of the teachings herein. For instance, in some versions trigger (68) may be omitted and surgical instrument (50) may be activated by a controlled of a robotic system. In other versions, surgical instrument (50) may be activated when coupled to generator (20).

Further still, surgical instrument (50) may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein; U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; U.S. Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Waveguide-Transducer Interfaces

In some instances it may be useful to selectively couple a waveguide and/or a horn to transducer (100) via an interface. For instance, in some situations it may desirable to reuse the electrical components of transducer (100), such as the piezoelectric elements, while disposing of the mechanical components that may be rendered unclean during a procedure. Such configurations may permit transducer (100) to be secured within multi-piece handle assembly (60) while only the waveguide and horn are decoupleable via the interface. Alternatively, transducer (100) may be contained in a transducer unit that may be coupleable to a handle assembly. In such instances, the waveguide and horn may be secured to the handle assembly and transducer (100) may be coupled to the waveguide and horn via the interface when the transducer unit is coupled to the handle assembly. Accordingly, various interfaces for coupling a waveguide to transducer (100) will be described below.

A. Exemplary V-Shaped Slot Interface

FIGS. 2-4 depict an exemplary V-shaped slot interface (200) for coupling a transducer assembly (210) to a waveguide assembly (250). Referring initially to FIG. 2, transducer assembly (210) comprises a plurality of piezoelectric elements (212) that are compressed between a first resonator (214) and a second resonator (220) to form a stack of piezoelectric elements. Piezoelectric elements (212) may be fabricated from any suitable material, for example, lead zirconate-titanate, lead meta-niobate, lead titanate, and/or any other suitable piezoelectric crystal material. Transducer assembly (210) further comprises electrodes (not shown), including at least one positive electrode and at least one negative electrode, that are configured to create a voltage potential across piezoelectric elements (212), such that piezoelectric elements (212) convert the electrical power into ultrasonic vibrations. In some versions the electrodes are coupled to a power source (not shown) that is external to a handle assembly (not shown) in which transducer assembly (210) is contained. In other versions, the power source may be contained within the handle assembly such that transducer assembly (210), the handle assembly, and the power source form a single reusable and/or reclaimable assembly. The ultrasonic vibrations produced by transducer assembly (210) are transmittable to a blade (not shown) via waveguide assembly (250), as will be described below. In the present example, first resonator (214) comprises a V-shaped female slot (230) formed in a distal end of first resonator (214). As shown in FIG. 3, V-shaped female slot (230) comprises a web channel (232) and a sector portion (234) (shown in phantom). Web channel (232) is a substantially vertical slot formed in a distal face (216) of first resonator (214) while sector portion (234) is a sector shaped recess that is offset from a distal face (216) of first resonator (214) by a distance d shown in FIG. 2. Of course other configurations for transducer assembly (210) will be apparent to one of ordinary skill in the art in view of the teachings herein.

Referring back to FIG. 2, waveguide assembly (250) includes a waveguide portion (252) and a horn portion (254). In the present example waveguide portion (252) and horn portion (254) are integral parts forming a monolithic waveguide assembly (250). It should be understood that in some versions horn portion (254) and waveguide portion (252) may also be separable, though this is merely optional. Of course, it should be understood that horn (254) may be integral with transducer assembly (210) such that waveguide assembly (250) selectively couples with horn (254). Such coupling of horn (254) to waveguide assembly (250) may incorporate any of the interfaces described herein. In the present example, horn portion (254) comprises a cylindrical section having a proximal face (256) and a flared section extending distally from the cylindrical section. Waveguide portion (252) comprises an elongate rod extending distally from the flared section of horn portion (254). In some versions waveguide assembly (250) may be made from titanium, though it should be understood that other metals may be used, including steel, aluminium, brass, etc. Horn portion (254) further comprises a V-shaped male connector (260), shown in FIG. 4. V-shaped male connector (260) comprises a web (262) and a sector (264). Web (262) extends proximally from proximal face (256) of horn portion (254) and is configured to fit in web channel (232) of V-shaped female slot (230). Sector (264) is formed on a proximal end of Web (262) and is configured to fit in sector portion (234) of V-shaped female slot (230). In some versions, web (262) extends proximally for a distance less than distance d, shown in FIG. 2, such that insertion of V-shaped male connector (260) into V-shaped female slot (230) creates a tight fit. Furthermore, waveguide assembly (250) may be included in a transmission assembly, such as transmission assembly (70) described above. Still further alternative versions for waveguide assembly (250) will be apparent to one of ordinary skill in the art in view of the teachings herein.

As shown in FIG. 2, transducer assembly (210) interfaces with waveguide assembly (250) at distal face (216) of first resonator (214) and proximal face (256) of horn portion (254). The proximal face (256)-distal face (216) longitudinal interface may be predetermined to substantially correspond to an antinode of the ultrasonic vibration wave produced by transducer assembly (210). An antinode is a point where the displacement due to the ultrasonic vibration wave is at a maximum. Alternatively, the antinode may be longitudinally located at the interface of the proximal face of sector (264) and the distal face of sector portion (234). Further still, the antinode may instead be longitudinally located in web (262) or in sector (264). Of course the antinode need not necessarily be located at any of these locations. In some versions the interface may correspond to a node, a point where the displacement due to the ultrasonic vibration wave is at zero, at any of the foregoing locations. In yet other versions, the interface may be located anywhere between a node and an antinode.

Initially, waveguide assembly (250) and transducer assembly (210) are decoupled, as shown separately in FIGS. 3-4. To couple waveguide assembly (250) to transducer assembly (210), the user vertically aligns V-shaped male connector (260) with V-shaped female slot (230). The user then slides V-shaped male connector (260) into V-shaped female slot (230), thereby coupling waveguide assembly (250) to transducer assembly (210). In some instances, V-shaped female slot (230) may retain V-shaped male connector (260) therein via a friction fit, a snap fit, detents, and/or any other connection mechanism as will be apparent to one of ordinary skill in the art in view of the teachings herein. The user may then use the assembled transducer and waveguide for further assembly of a surgical instrument, or, if the surgical instrument is fully assembled, the user may utilize the surgical instrument for a procedure. To decouple waveguide assembly (250) and transducer assembly (210), the user slides V-shaped male connector (260) out of V-shaped female slot (230). Waveguide assembly (250) may then be disposed of, cleaned, resterilized, and/or otherwise. Transducer assembly (210) may be reused, cleaned, reclaimed, and/or otherwise as well. Thus, a user may dispose of the unclean mechanical components of waveguide assembly (250) while recycling the electrical components of transducer assembly (210).

Of course other configurations for V-shaped slot interface (200) will be apparent to one of ordinary skill in the art in view of the teachings herein. For instance, V-shaped male connector (260) and V-shaped female slot (230) may be inverted, and transducer assembly (210) may be coupled to transducer unit (800) described below in section IV and shown in FIG. 18.

B. Exemplary Rotatable Ovular Interface

Figure 5:
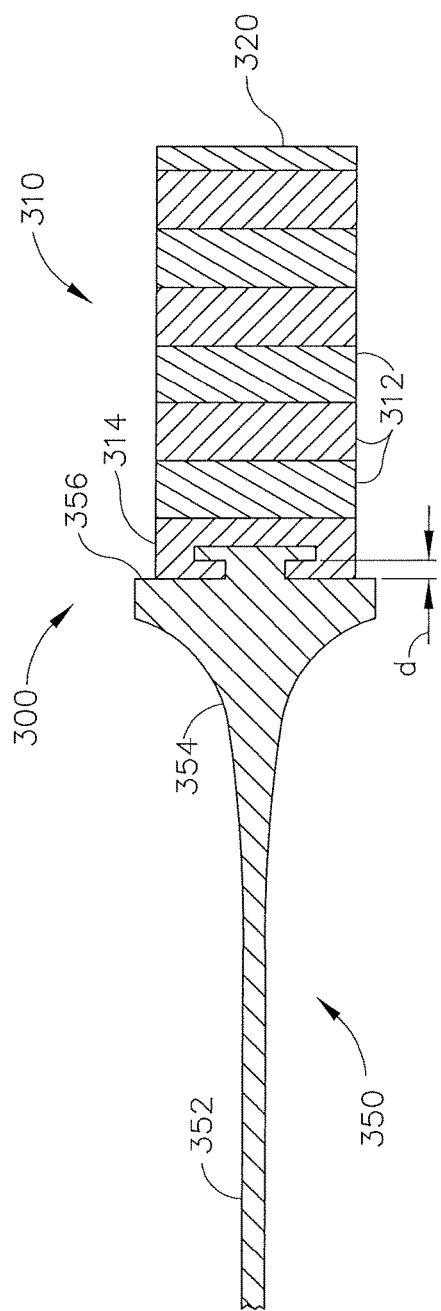
FIG. 5 depicts a top cross-sectional view of an exemplary alternative transducer assembly and waveguide assembly coupled together via a rotatable ovular interface.
Figure 7:
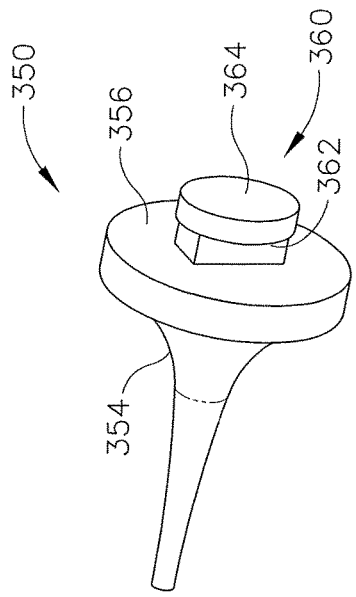
FIG. 7 depicts a rear partial perspective view of the waveguide of FIG. 5; showing an ovular male connector.
Figure 6:
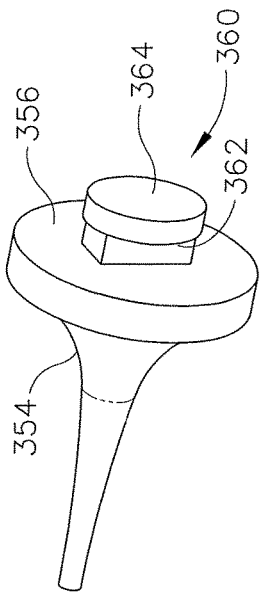
FIG. 6 depicts a front elevation view of the transducer of FIG. 5 showing an ovular aperture and an offset cylindrical recess.

FIGS. 5-7 depict an exemplary rotatable ovular interface (300) for coupling a transducer assembly (310) to a waveguide assembly (350). Referring initially to FIG. 5, transducer assembly (310) comprises a plurality of piezoelectric elements (312) that are compressed between a first resonator (314) and a second resonator (320) to form a stack of piezoelectric elements. Piezoelectric elements (312) may be fabricated from any suitable material, for example, lead zirconate-titanate, lead meta-niobate, lead titanate, and/or any other suitable piezoelectric crystal material. Transducer assembly (310) further comprises electrodes (not shown), including at least one positive electrode and at least one negative electrode, that are configured to create a voltage potential across piezoelectric elements (312), such that piezoelectric elements (312) convert the electrical power into ultrasonic vibrations. In some versions the electrodes are coupled to a power source (not shown) that is external to a handle assembly (not shown) in which transducer assembly (310) is contained. In other versions, the power source may be contained within the handle assembly such that transducer assembly (310), the handle assembly, and the power source form a single reusable and/or reclaimable assembly. The ultrasonic vibrations produced by transducer assembly (310) are transmittable to a blade (not shown) via waveguide assembly (350), as will be described below. In the example shown in FIG. 6, first resonator (314) comprises an ovular aperture (330) formed through a distal face (316) of first resonator (314) and a cylindrical recess (332) (shown in phantom) located proximally of ovular aperture (330). Cylindrical recess (332) is offset from distal face (316) of first resonator (314) by a distance d shown in FIG. 5 and has a diameter substantially equal to the major axis diameter of ovular aperture (330). While the present example includes an ovular aperture (330), it should be understood that other shapes and sizes for aperture (330) may be used. For instance, a rectangular aperture, a T-shaped aperture, a triangular aperture, an S-shaped aperture, an egg shaped aperture, an irregularly shaped aperture, and/or any other asymmetrical aperture may be used. Of course other configurations for transducer assembly (310) will be apparent to one of ordinary skill in the art in view of the teachings herein.

Referring back to FIG. 5, waveguide assembly (350) includes a waveguide portion (352) and a horn portion (354). In the present example waveguide portion (352) and horn portion (354) are integral parts forming a monolithic waveguide assembly (350). It should be understood that in some versions horn portion (354) and waveguide portion (352) may also be separable, though this is merely optional. Of course, it should be understood that horn portion (354) may be integral with transducer assembly (310) such that waveguide assembly (350) selectively couples with horn portion (354). Such coupling of horn portion (354) to waveguide assembly (350) may incorporate any of the interfaces described herein. In the present example, horn portion (354) comprises a cylindrical section having a proximal face (356) and a flared section extending distally from the cylindrical section. Waveguide portion (352) comprises an elongate rod extending distally from the flared section of horn portion (354). In some versions waveguide assembly (350) may be made from titanium, though it should be understood that other metals may be used, including steel, aluminium, brass, etc. Horn portion (354) further comprises an ovular male connector (360), shown in FIG. 7. Ovular male connector (360) comprises a web (362) and an elliptic disc (364). Web (362) extends proximally from proximal face (356) of horn portion (354). Elliptic disc (364) is formed on a proximal end of web (362) and is configured to be insertable through ovular aperture (330) and into cylindrical recess (332). In some versions, web (362) extends proximally for a distance less than distance d, shown in FIG. 5, such that insertion and subsequent rotation of elliptic disc (364) through ovular aperture (330) and into cylindrical recess (332) creates tight fit. Furthermore, waveguide assembly (350) may be included in a transmission assembly, such as transmission assembly (70) described above. Still further alternative versions for waveguide assembly (350) will be apparent to one of ordinary skill in the art in view of the teachings herein.

As shown in FIG. 5, transducer assembly (310) interfaces with waveguide assembly (350) at distal face (316) of first resonator (314) and proximal face (356) of horn portion (354). The proximal face (356)-distal face (316) longitudinal interface may be predetermined to substantially correspond to an antinode of the ultrasonic vibration wave produced by transducer assembly (310). An antinode is a point where the displacement due to the ultrasonic vibration wave is at a maximum. Alternatively, the antinode may be longitudinally located at the interface of the proximal face of elliptic cylinder (364) and the distal face of cylindrical recess (332). Further still, the antinode may instead be longitudinally located in shaft (362) or in elliptic cylinder (364). Of course the antinode need not necessarily be located at any of these locations. In some versions the interface may correspond to a node, a point where the displacement due to the ultrasonic vibration wave is at zero, at any of the foregoing locations. In yet other versions, the interface may be located anywhere between a node and an antinode.

Initially, waveguide assembly (350) and transducer assembly (310) are decoupled, as shown separately in FIGS. 6-7. To couple waveguide assembly (350) to transducer assembly (310), the user inserts elliptic cylinder (364) through ovular aperture (330) and into cylindrical recess (332). The user then rotates waveguide assembly (350) such that elliptic cylinder (364) is no longer aligned with ovular aperture (330), thereby coupling waveguide assembly (350) to transducer assembly (310). By way of example only, the user may rotate waveguide assembly (350) by 90 degrees, or a one-quarter turn. Of course any other suitable rotational angles may be used in the present example. If an asymmetrical component is used instead of elliptic cylinder (364), rotational angles greater than 0 and less than 360 may be used. In some instances, cylindrical recess (332) may retain elliptic cylinder (364) therein via a friction fit, a snap fit, detents, and/or any other connection mechanism as will be apparent to one of ordinary skill in the art in view of the teachings herein. Such connection mechanisms may be operable to maintain waveguide assembly (350) in a predetermined orientation relative to transducer assembly (310). The user may then use the assembled transducer and waveguide for further assembly of a surgical instrument, or, if the surgical instrument is fully assembled, the user may utilize the surgical instrument for a procedure. To decouple waveguide assembly (350) and transducer assembly (310), the user rotates waveguide assembly (350) until elliptic cylinder (364) is aligned with ovular aperture (330). In some versions, waveguide assembly (350) and/or transducer assembly (310) may have indicators (not shown), such as visual markings, to indicate when elliptic cylinder (364) and ovular aperture (330) are aligned. With elliptic cylinder (364) and ovular aperture (330) aligned, the user pulls waveguide assembly (350) distally to decouple waveguide assembly (350) from transducer assembly (310). Waveguide assembly (350) may then be disposed of, cleaned, resterilized, and/or otherwise. Transducer assembly (310) may be reused, cleaned, reclaimed, and/or otherwise as well. Thus, a user may dispose of the unclean mechanical components of waveguide assembly (350) while recycling the electrical components of transducer assembly (310). Of course other configurations for rotatable ovular interface (300) will be apparent to one of ordinary skill in the art in view of the teachings herein.

Figure 9:
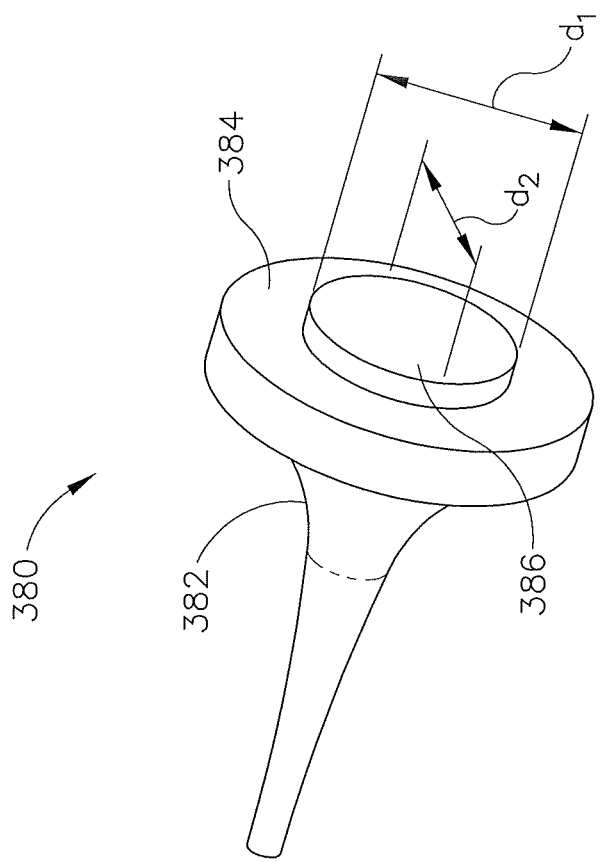
FIG. 9 depicts a rear partial perspective view of a waveguide assembly of the rotatable ovular interface of FIG. 8 showing an elliptic cylinder.
Figure 8:
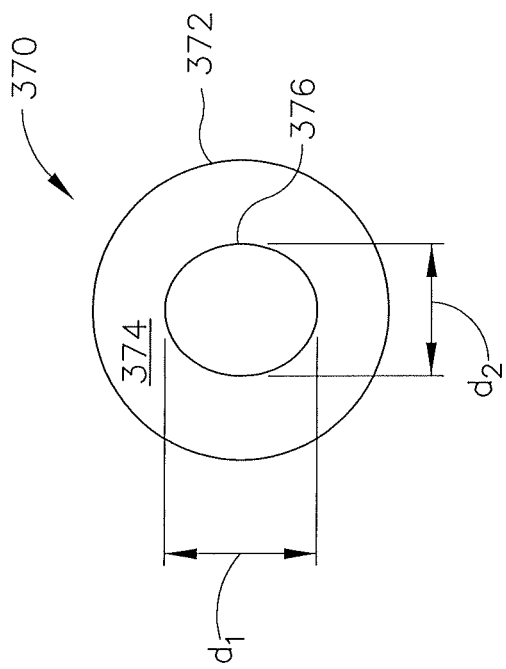
FIG. 8 depicts a front elevation view of a transducer assembly of an exemplary alternative rotatable ovular interface showing an ovular recess.

FIG. 8 shows an exemplary alternative transducer assembly (370) comprising an ovular recess (376) formed in a distal face (374) of first resonator (372). Ovular recess (376) of the present example has a major axis of diameter d1 and a minor axis of diameter d2. As shown, d1 is slightly larger than d2. By way of example only, d1 may be approximately 0.255 and d2 may be approximately 0.250. FIG. 9 shows an exemplary alternative waveguide assembly (380) comprising a waveguide portion (not shown) and a horn portion (382). Horn portion (382) comprises an elliptic cylinder (386) projecting proximally from a proximal face (384) of horn portion (382). Elliptic cylinder (386) also has a major axis of diameter d1 and a minor axis of diameter d2, where d1 is slightly larger than d2. In the present example, d1 of elliptic cylinder (386) is substantially equal to d1 of ovular recess (376) and d2 of elliptic cylinder (386) is substantially equal to d2 of ovular recess (376).

Initially, waveguide assembly (380) and transducer assembly (370) are decoupled, as shown separately in FIGS. 8-9. To couple waveguide assembly (380) to transducer assembly (380), the user aligns and inserts elliptic cylinder (386) into ovular recess (376). The user then rotates waveguide assembly (380) such that elliptic cylinder (386) frictionally fits in ovular recess (376), thereby coupling waveguide assembly (380) to transducer assembly (370). As will be appreciated by one of ordinary skill in the art, when elliptic cylinder (386) is rotated 90 degrees, or a quarter turn, major axis of elliptic cylinder (386) having a diameter d1 forms a frictional fit within minor axis of ovular recess (376) having a slightly smaller diameter d2. Of course other rotational angles may be possible as well to form a frictional fit. The user may then use the assembled transducer and waveguide for further assembly of a surgical instrument, or, if the surgical instrument is fully assembled, the user may utilize the surgical instrument for a procedure. To decouple waveguide assembly (380) and transducer assembly (370), the user rotates waveguide assembly (380) until the major axis of elliptic cylinder (386) is aligned with the major axis of ovular recess (376). In some versions, waveguide assembly (380) and/or transducer assembly (370) may have indicators (not shown), such as visual markings, to indicate when elliptic cylinder (386) and ovular recess (376) are aligned. With elliptic cylinder (386) and ovular recess (376) aligned, the user pulls waveguide assembly (380) distally to decouple waveguide assembly (380) from transducer assembly (370). Waveguide assembly (380) may then be disposed of, cleaned, resterilized, and/or otherwise. Transducer assembly (370) may be reused, cleaned, reclaimed, and/or otherwise as well. Thus, a user may dispose of the unclean mechanical components of waveguide assembly (380) while recycling the electrical components of transducer assembly (370).

While the foregoing example described the frictional fit in relation to elliptic cylinder (386) and ovular recess (376), other rotationally asymmetric configurations may be used as well.

C. Exemplary Interference Fit Interface

Figure 10:
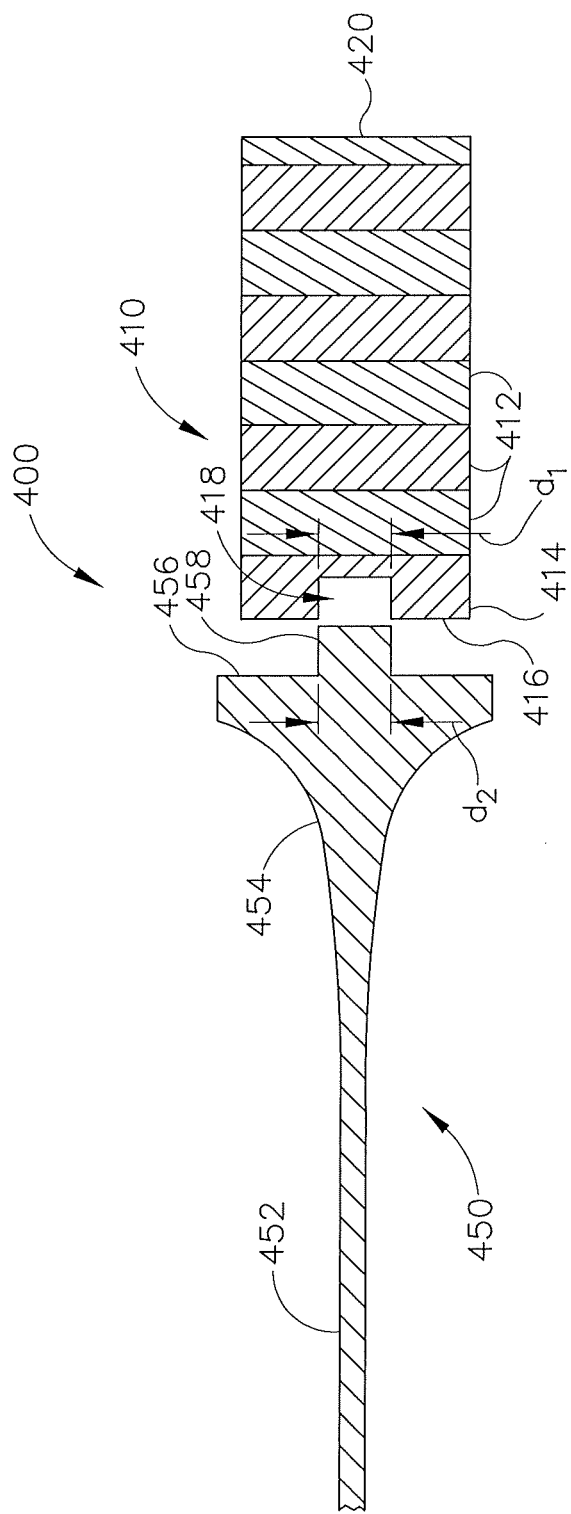
FIG. 10 depicts a top cross-sectional view of another exemplary transducer assembly and waveguide assembly configured to couple together via an interference fit interface.

FIG. 10 depicts an exemplary interference fit interface (400) for coupling a transducer assembly (410) to a waveguide assembly (450). Transducer assembly (410) comprises a plurality of piezoelectric elements (412) that are compressed between a first resonator (414) and a second resonator (420) to form a stack of piezoelectric elements. Piezoelectric elements (412) may be fabricated from any suitable material, for example, lead zirconate-titanate, lead metaniobate, lead titanate, and/or any other suitable piezoelectric crystal material. Transducer assembly (410) further comprises electrodes (not shown), including at least one positive electrode and at least one negative electrode, that are configured to create a voltage potential across piezoelectric elements (412), such that piezoelectric elements (412) convert the electrical power into ultrasonic vibrations. In some versions the electrodes are coupled to a power source (not shown) that is external to a handle assembly (not shown) in which transducer assembly (410) is contained. In other versions, the power source may be contained within the handle assembly such that transducer assembly (410), the handle assembly, and the power source form a single reusable and/or reclaimable assembly. The ultrasonic vibration produced by transducer assembly (410) are transmittable to a blade (not shown) via waveguide assembly (450), as will be described below. As shown in the example in FIG. 10, first resonator (414) comprises a cylindrical recess (418) formed in a distal face (416) of first resonator (414). Recess (418) of the present example has a diameter d1. While the present example includes a cylindrical recess (418), it should be understood that other shapes and/or sizes for recess (418) may be used. For instance, a cuboid recess, an elliptic cylindrical recess, and/or any other shaped recess may be used. Of course other configurations for transducer assembly (410) will be apparent to one of ordinary skill in the art in view of the teachings herein.

Waveguide assembly (450) includes a waveguide portion (452) and a horn portion (454). In the present example waveguide portion (452) and horn portion (454) are integral parts forming a monolithic waveguide assembly (450). It should be understood that in some versions horn portion (454) and waveguide portion (452) may also be separable, though this is merely optional. Of course, it should be understood that horn portion (454) may be integral with transducer assembly (410) such that waveguide assembly (450) selectively couples with horn portion (454). Such coupling of horn portion (454) to waveguide assembly (450) may incorporate any of the interfaces described herein. In the present example, horn portion (454) comprises a cylindrical section having a proximal face (456) and a flared section extending distally from the cylindrical section. Waveguide portion (452) comprises an elongate rod extending distally from the flared section of horn portion (454). In some versions waveguide assembly (450) may be made from titanium, though it should be understood that other metals may be used, including steel, aluminium, brass, etc. Horn portion (454) of the present example further comprises a cylindrical pin (458) having a diameter d2. Cylindrical pin (458) extends proximally from proximal face (456) of horn portion (454). As shown in FIG. 10, the diameter d2 of cylindrical pin (458) is slightly larger than diameter d1 of cylindrical recess (418) of first resonator (414). Cylindrical pin (458) is configured to be insertable into cylindrical recess (418) despite this size diametric size differential, as will be discussed below. In some versions, waveguide assembly (450) may have a recess and transducer assembly (410) may have a pin. Furthermore, waveguide assembly (450) may be included in a transmission assembly, such as transmission assembly (70) described above. Still further alternative versions for waveguide assembly (450) will be apparent to one of ordinary skill in the art in view of the teachings herein.

As shown in FIG. 10, transducer assembly (410) interfaces with waveguide assembly (450) at distal face (416) of first resonator (414) and proximal face (456) of horn portion (454). The proximal face (456)-distal face (416) longitudinal interface may be predetermined to substantially correspond to an antinode of the ultrasonic vibration wave produced by transducer assembly (410). An antinode is a point where the displacement due to the ultrasonic vibration wave is at a maximum. Alternatively, the antinode may be longitudinally located at the interface of the proximal face cylindrical pin (458) and the distal face of cylindrical recess (418). Further still, the antinode may instead be longitudinally located within cylindrical pin (458). Of course the antinode need not necessarily be located at any of these locations. In some versions the interface may correspond to a node, a point where the displacement due to the ultrasonic vibration wave is at zero, at any of the foregoing locations. In yet other versions, the interface may be located anywhere between a node and an antinode.

When a user desires to couple waveguide assembly (450) to transducer assembly (410), initially the user aligns cylindrical pin (458) with cylindrical recess (418). In some versions, the user activates transducer assembly (410) and the oscillations produced by transducer assembly (410) at first resonator (414) may cause the matrix of molecules of first resonator (414) to expand and/or contract according to Poisson's ratio. Such expansion and/or contraction may permit a user to insert cylindrical pin (458) into cylindrical recess (418). In other versions, the oscillations produced by transducer assembly (410) may thermally heat first resonator (414), thereby softening and/or potentially expanding cylindrical recess (418) to permit insertion of cylindrical pin (458) therein. Once transducer assembly (410) is deactivated, an interference fit is formed between cylindrical pin (458) and cylindrical recess (418) due to the diametric difference between d1 and d2. Alternatively, waveguide assembly (450) and/or cylindrical pin (458) may be super-cooled, such as through the use of dry ice, liquid nitrogen, refrigeration, or other temperature reducing means, to shrink cylindrical pin (458) for insertion into cylindrical recess (418). Once cylindrical pin (458) heats back up, an interference fit is formed between cylindrical pin (458) and cylindrical recess (418) due to the diametric difference between d1 and d2. Of course users may super-cool waveguide assembly (450) and/or transducer assembly (410) and thermally heat the other. In still other versions the user may simply be able to force cylindrical pin (458) into cylindrical recess (418) without activating transducer assembly (410) to frictionally fit waveguide assembly (450) to transducer assembly (410). Of course other methods for producing an interference fit between cylindrical pin (458) and cylindrical recess (418) will be apparent to one of ordinary skill in the art in view of the teachings herein.

With waveguide assembly (450) coupled to transducer assembly (410), the user may then use the assembled transducer and waveguide for further assembly of a surgical instrument, or, if the surgical instrument is fully assembled, the user may utilize the surgical instrument for a procedure. To decouple waveguide assembly (450) from transducer assembly (410), the user may simply pull upon waveguide assembly (450) proximally, activate transducer assembly (410) and pull upon waveguide assembly (450) proximally, and/or thermally heat and/or cool waveguide assembly (450) and/or transducer assembly (410) and pull upon waveguide assembly (450) proximally. Waveguide assembly (450) may then be disposed of, cleaned, resterilized, and/or otherwise. Transducer assembly (410) may be reused, cleaned, reclaimed, and/or otherwise as well. Thus, a user may dispose of the unclean mechanical components of waveguide assembly (450) while recycling the electrical components of transducer assembly (410).

Of course other configurations for interference fit coupling mechanism (400) will be apparent to one of ordinary skill in the art in view of the teachings herein.

D. Exemplary Ball Joint and Cam Interface

FIGS. 11-14 depict an exemplary ball joint interface (500) for coupling a transducer assembly (510) to a waveguide assembly (550). Referring initially to FIG. 11, transducer assembly (510) comprises a plurality of piezoelectric elements (512) that are compressed between a first resonator (514) and a second resonator (520) to form a stack of piezoelectric elements. Piezoelectric elements (512) may be fabricated from any suitable material, for example, lead zirconate-titanate, lead meta-niobate, lead titanate, and/or any other suitable piezoelectric crystal material. Transducer assembly (510) further comprises electrodes (not shown), including at least one positive electrode and at least one negative electrode, that are configured to create a voltage potential across piezoelectric elements (512), such that piezoelectric elements (512) convert the electrical power into ultrasonic vibrations. In some versions the electrodes are coupled to a power source (not shown) that is external to a handle assembly (not shown) in which transducer assembly (510) is contained. In other versions, the power source may be contained within the handle assembly such that transducer assembly (510), the handle assembly, and the power source form a single reusable and/or reclaimable assembly. The ultrasonic vibrations produced by transmission assembly (510) are transmittable to a blade (not shown) via waveguide assembly (550), as will be described below. In the present example, first resonator (514) comprises a cup feature (530) formed in a distal end of first resonator (514). As shown in FIG. 12, cup feature (530) comprises a ball shaft portion (532) (shown in phantom), a ball cup (534) (shown in phantom), and an arcuate slot portion (536). Ball shaft portion (532) is a substantially vertical recess sized to receive ball (564), and ball shaft portion (532) is formed in first resonator (514) at a distance from a distal face (516) of first resonator (514) that is substantially equal to the combined length of shaft (562) and a radius of ball (564) described below. It should be understood that ball shaft portion (532) may alternatively be an angled shaft, such as angled ball shaft portion (576) shown in FIG. 15. Ball shaft portion (532) terminates at the bottom with ball cup (534) configured to receive a portion of ball (564) therein. In some versions, ball cup (534) may include detents (not shown) or other features for ball (564) to snap into ball cup (534) and be retained therein. Arcuate slot portion (536) is a slot formed by cutting a sector out of first resonator (514) angularly spanning from ball shaft portion (532) to a longitudinal axis of transducer assembly (510). In the example shown, arcuate slot portion (536) is a 90 degree sector slot sized to permit shaft (562) to rotate from the vertical to the horizontal through arcuate slot portion (536); but also sized to prevent ball (564) from entering arcuate slot portion (536). First resonator (514) of the present example includes a rounded portion (518) configured to permit rotation of waveguide assembly (550) about first resonator (514) while ball (564) is inserted into ball cup (534). In some versions, rounded portion (518) may also cam waveguide assembly (550) distally to create an increasingly tight fit as waveguide assembly (550) is rotated from the vertical to the horizontal. In addition or in the alternative, ball (564) may be asymmetric or have a camming portion such that an increasingly tight fit is created when waveguide assembly (550) is rotated from the vertical to the horizontal. In the foregoing configuration, rounded portion (518) need not necessarily cam waveguide assembly (550). Of course other configurations for transducer assembly (510) will be apparent to one of ordinary skill in the art in view of the teachings herein.

Referring back to FIG. 11, waveguide assembly (550) includes a waveguide portion (552) and a horn portion (554). In the present example waveguide portion (552) and horn portion (554) are integral parts forming a monolithic waveguide assembly (550). It should be understood that in some versions horn portion (554) and waveguide portion (552) may also be separable, though this is merely optional. Of course, it should be understood that horn portion (554) may be integral with transducer assembly (510) such that waveguide assembly (550) selectively couples with horn portion (554). Such coupling of horn portion (554) to waveguide assembly (550) may incorporate any of the interfaces described herein. In the present example, horn portion (554) comprises a cylindrical section having a proximal face (556) and a flared section extending distally from the cylindrical section. Waveguide portion (552) comprises an elongate rod extending distally from the flared section of horn portion (554). In some versions waveguide assembly (550) may be made from titanium, though it should be understood that other metals may be used, including steel, aluminium, brass, etc. Horn portion (554) further comprises a ball connector (560), shown in FIG. 13. Ball connector (560) comprises a shaft (562) and a ball (564). Shaft (562) extends proximally from proximal face (556) of horn portion (554). Ball (564) is formed on a proximal end of shaft (562) and is configured to be insertable vertically into ball shaft portion (532) of cup feature (530) when waveguide assembly (550) is vertically oriented relative to transducer assembly (510). When ball (564) is so inserted, waveguide assembly (550) may be rotated to the horizontal axis such that shaft (562) is rotated through arcuate slot portion (536) to couple waveguide assembly (550) to transducer assembly (510). In the example shown in FIG. 11, waveguide assembly (550) is rotated counterclockwise, though this is merely exemplary. Furthermore, waveguide assembly (550) may be included in a transmission assembly, such as transmission assembly (70) described above. Still further alternative versions for waveguide assembly (550) will be apparent to one of ordinary skill in the art in view of the teachings herein. For instance, in the example shown in FIG. 14, shaft (562) includes a tapered ridge (566) extending from shaft (562) such that shaft (562) is asymmetric and has a cross-sectional profile shaped like a teardrop. Accordingly, waveguide assembly (550) may only be insertable in a single orientation in this example.

Initially, waveguide assembly (550) and transducer assembly (510) are decoupled, as shown separately in FIGS. 12-13. To couple waveguide assembly (550) to transducer assembly (510), the user orients waveguide assembly (550) vertically and aligns ball connector (560) with ball shaft portion (532) of cup feature (530). The user inserts ball (564) into ball cup (534) then rotates waveguide assembly (550) such that shaft (562) rotates through arcuate slot portion (536) until waveguide assembly (550) is longitudinally aligned with transducer assembly (510), thereby coupling waveguide assembly (550) to transducer assembly (510). The user may then use the assembled transducer and waveguide for further assembly of a surgical instrument, or, if the surgical instrument is fully assembled, the user may utilize the surgical instrument for a procedure. To decouple waveguide assembly (550) and transducer assembly (510), the user rotates waveguide assembly (550) to a vertical position such that the user can lift ball (564) out of ball cup (534) and out of ball shaft portion (532). Waveguide assembly (550) may then be disposed of, cleaned, resterilized, and/or otherwise. Transducer assembly (510) may be reused, cleaned, reclaimed, and/or otherwise as well. Thus, a user may dispose of the unclean mechanical components of waveguide assembly (550) while recycling the electrical components of transducer assembly (510).

Figure 15:
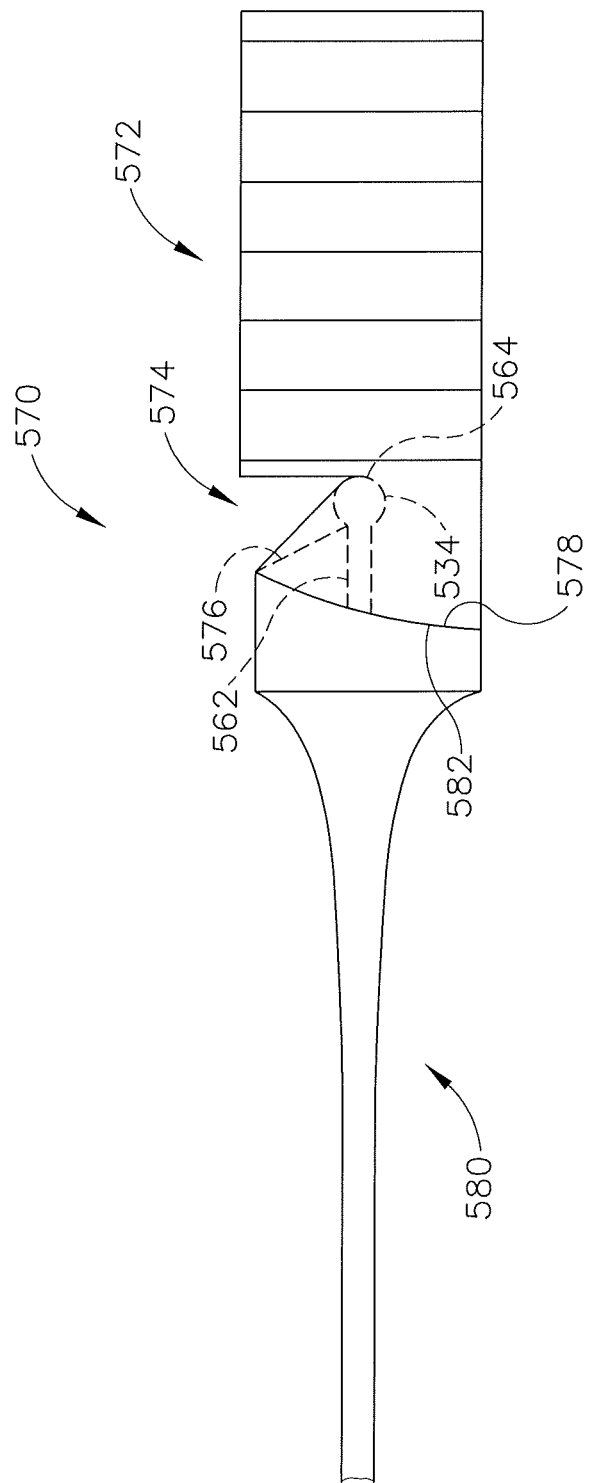
FIG. 15 depicts a side elevation view of an exemplary alternative ball joint interface having cammed ends.

Of course other configurations for ball joint interface (500) will be apparent to one of ordinary skill in the art in view of the teachings herein. For instance, an alternative ball joint interface (570) is shown in FIG. 15. In the example shown, transducer assembly (572) includes a notch (574), an angled ball shaft portion (576) (shown in phantom), ball cup (534), an arcuate slot portion (not shown), and a cammed distal end (578). The arcuate slot portion is configured in a substantially similar manner to arcuate slot portion (536). Waveguide assembly (580) is configured in a substantially similar manner to waveguide assembly (550), except waveguide assembly (580) includes a cammed proximal end (582) that is complementary to cammed distal end (578). In the present example, the user inserts ball (564) into ball cup (534) then rotates waveguide assembly (580) to the horizontal axis by rotating cammed proximal end (582) along cammed distal end (578) while shaft (562) is guided through arcuate slot portion. Cammed proximal end (582) and cammed distal end (578) may be configured such that ball (564) is urged distally against ball cup (534) or into a pocket (not shown) formed distally of ball cup (534). The user may then use the assembled transducer and waveguide for further assembly of a surgical instrument, or, if the surgical instrument is fully assembled, the user may utilize the surgical instrument for a procedure. To decouple waveguide assembly (580) and transducer assembly (572), the user rotates waveguide assembly (580) to a position such that the user can lift ball (564) out of ball cup (534) and out of angled ball shaft portion (576).

While some examples of interfaces for transmission assemblies and waveguide assemblies have been described herein, still other interfaces will be apparent to one of ordinary skill in the art in view of the teachings herein.

III. Exemplary Gear-Driven Coupling Mechanism

In some other instances it may be useful to selectively couple a waveguide to transducer (100) using a mechanism that can have predetermined characteristics such that the torquing of transducer (100) onto waveguide may be predictable. Such mechanisms may enable the implementation of coupling assemblies for transducer (100) and the waveguide that may be easier to operate, because a user may simply need to operate the coupling assembly from an uncoupled position to a coupled position. Alternatively, such mechanisms with predetermined characteristics may provide a predictability for torquing transducer (100) onto the waveguide at a variety of torque values. In addition, such coupling mechanisms may be included in a separable unit such that transducer (100) may be reused with the coupling mechanism while the other components may be disposed of. Accordingly, a merely exemplary gear-driven coupling mechanism will be described below.

Figure 16:
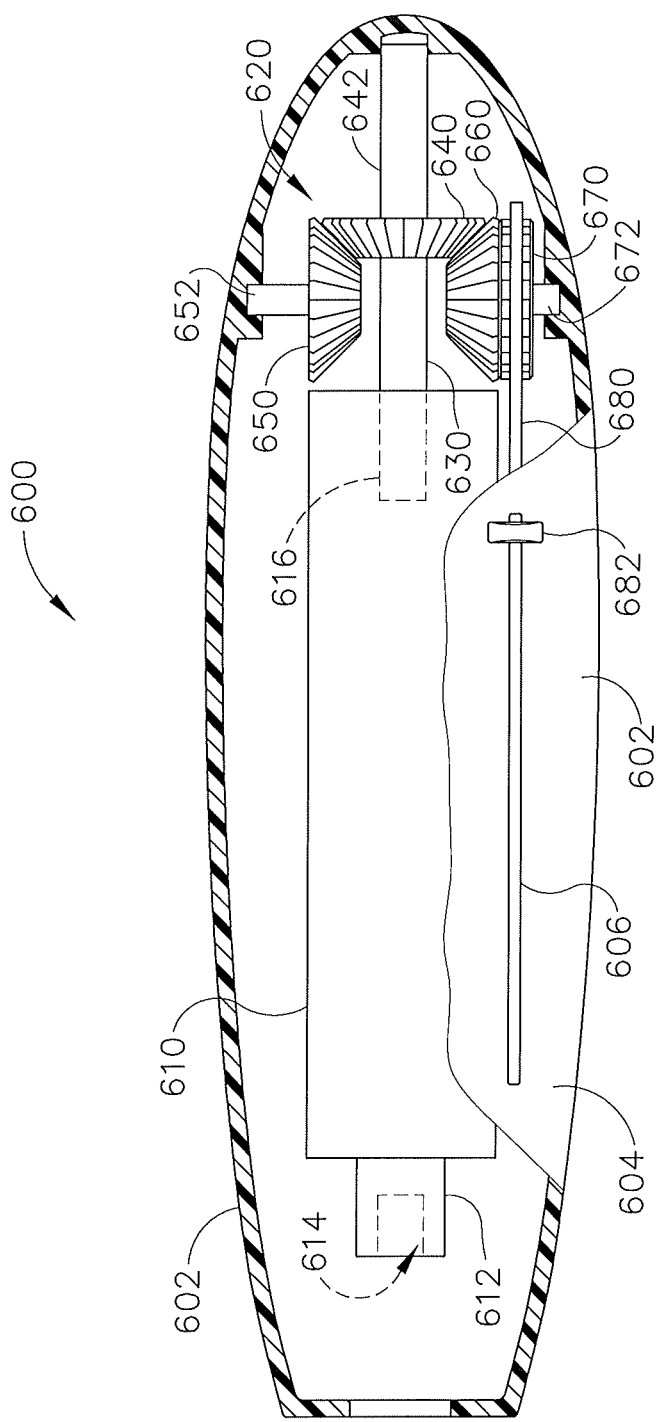
FIG. 16 depicts a top plan view of an exemplary transducer unit with a portion of the casing removed and showing a transducer, a rack gear, a pinion gear, and a plurality of bevel gears for rotating the transducer.

FIG. 16 depicts a top plan view of an exemplary transducer unit (600) with a portion of a casing (602) removed to show some of the internal components therein. In the present example, transducer unit (600) includes a casing (602), a transducer (610), and a geared mechanism (620). In the present example, transducer (610) includes a horn (612) having a distal threaded recess (614) (shown in phantom) configured to couple with threading (732) on waveguide (730), described in more detail below and shown in FIGS. 17A-17C. Transducer (610) also includes a proximal recess (616) (shown in phantom) coupled to a transducer shaft (630), as will be described below as well. Transducer (610) is rotatably coupled to casing (602) via one or more bearing members (not shown) such that transducer (610) may both translate longitudinally and rotate about a longitudinal axis of transducer (610) while still being coupled to casing (602). Casing (602) may further include attachment features (not shown) such that casing (602) may be coupled to lower handle portion (700) described below, thought this is merely optional. Such attachment features may include snap fasteners, clips, clamps, screws, bolts, interference fittings, latches, etc. Alternatively, transducer unit (600) may include a slide lock assembly, such as slide lock assembly (820) described below in section IV and shown in FIG. 18.

Geared mechanism (620) of the present example comprises a transducer shaft (630), a rear bevel gear (640), a support bevel gear (650), and a main bevel gear (660). Main bevel gear (660) is fixedly coupled to a pinion gear (670), though it should be understood that pinion gear (670) and main bevel gear (660) may be integrally formed to be a single gear. A rack gear (680) is slidably mounted to a portion (604) of casing (602) via a longitudinal slot (606) formed in portion (604) and a handle (682) coupled to a distal end of rack gear (680) located outside of casing (602). It should be noted that portion (604) is not separate from casing (602); rather, for ease of viewing and explanation, portion (604) has been provided as context for slot (606). Transducer shaft (630) of the present example is insertable into proximal recess (616) of transducer (610) and is affixed to transducer (610). Transducer shaft (630) is also fixedly attached to rear bevel gear (640) such that rotation of rear bevel gear (640) rotates transducer shaft (630) (and therefore rotates transducer (610)). Rear bevel gear (640) of the present example is supported by and rotatable relative to a rear shaft (642) that is coupled casing (602). In some versions, rear shaft (642) may be affixed to rear bevel gear (640) and may extend out of casing (602) such that a manual knob (not shown) may be coupled to rear shaft (642) to manually rotate rear bevel gear (640) (and, consequently, transducer (610)). For instance, the manual knob may be provided to apply a final torque to transducer (610) when coupled to waveguide (730), or the manual knob may be used to initially break transducer (610) loose from waveguide (730) when decoupling transducer (610). Support bevel gear (650) meshes with rear bevel gear (640) to provide additional alignment and support for rear bevel gear (640). Support bevel gear (650) is supported by a support shaft (652) coupled to casing (602). In some versions, support shaft (652) may be coupled to support bevel gear (650) and may extend out of casing (602) such that another manual knob (not shown) may be coupled to support shaft (652) to manually rotate support bevel gear (650) (and, consequently, transducer (610)). In some versions, support bevel gear (650) simply acts as an idler gear. It should be understood that support bevel gear (650) is merely optional and may be omitted.

Main bevel gear (660) meshes with rear bevel gear (640) such that main bevel gear (660) is operable to rotate rear bevel gear (640). In the present example, main bevel gear (660) is fixedly coupled to pinion gear (670) such that rotation of pinion gear (670) rotates main bevel gear (660). Main bevel gear (660) and pinion gear (670) of the present example are supported by and rotatable about (or with) a pinion shaft (672) that is coupled casing (602). Rack gear (680) meshes with pinion gear (670) such that the linear motion of rack gear (680) is converted into rotation of pinion gear (670). In the present example, rack gear (680) is a flexible or semi-rigid member such that rack gear (680) may be bent into portions of lower handle portion (700) when transducer unit (600) is coupled thereto and rack gear (680) is in the uncoupled position. In some versions, rack gear (680) may instead be a rigid member that extends out an aperture in casing (602) when rack gear (680) is in an uncoupled position. A handle (682) is coupled to the distal end of rack gear (680) and is located on the outside of casing (602). Handle (682) of the present example is coupled to a shaft (not shown) at the distal end of rack gear (680) that is insertable through slot (606). Accordingly, with handle (682) located on the exterior of casing (602), a user may operate rack gear (680) within casing (602) simply by grasping handle (682) and actuating handle (682) longitudinally along slot (606). In some versions, slot (606) may have a proximal end defining an uncoupled position and a distal end defining a coupled position, as will be described in more detail below. Slot (606) may further include visual markings (not shown) indicating the uncoupled and coupled positions and/or various positional indicators along slot (606) indicating the rotational positions and/or torques applied to transducer (610) via transducer shaft (630). Of course other configurations for transducer unit (600) will be apparent to one of ordinary skill in the art in view of the teachings herein.

Referring now to FIG. 17A, transducer unit (600) is initially decoupled from a lower handle portion (700). Lower handle portion (700) includes a casing (702), a pair of toggle buttons (710), a rotation knob (720), a waveguide (730), and a trigger (740) pivotally mounted to lower handle portion (700). Casing (702), toggle buttons (710), rotation knob (720), and/or trigger (740) may be configured in accordance with at least some of the teachings of casing (61), the toggle buttons, rotation knob (66), and/or trigger (68) described above or in accordance with U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660 (issued as U.S. Pat. No. 8,461,744); U.S. Pat. No. 6,500,176; U.S. Pat. Pub. No. 2011/0087218, now U.S. Pat. No. 8,939,974, issued Jan. 27, 2015; and/or U.S. Pat. Pub. No. 2009/0143797 (issued as U.S. Pat. No. 8,419,757). Casing (702) may further include attachment features (not shown) complementary to those of casing (602) such that casings (602, 702) may be coupled together, thought this is merely optional. Such attachment features may include snap fasteners, clips, clamps, screws, bolts, interference fittings, latches, etc. Alternatively, lower handle portion (700) may include slider recesses, such as slider recesses (854) described below in section IV and shown in FIG. 18. In the present example, waveguide (730) is slidable relative to rotation knob (720) with a portion of waveguide (730) extending distally from lower handle portion (700). In the present example, waveguide (730) is slidable relative to rotation knob (720) to permit waveguide (730) to screw into transducer (610), though this is merely optional. In some versions waveguide (730) may be affixed to rotation knob (720) and transducer (610) is slidable relative to casing (602). A proximal end of the present exemplary waveguide (730) extends proximally into casing (702) of lower handle assembly (700) and includes threading (732) configured to threadably couple to distal threaded recess (614) of transducer (610). An end effector (not shown), such as end effector (80), is coupled to a distal end of the waveguide (730) and is operable to simultaneously sever tissue and vaporize adjacent tissue cells, thereby providing a cauterizing effect with relatively little thermal spread. In the present example, rotation knob (720) may be selectively coupleable to waveguide (730) such that rotation knob (720) is operable to rotate waveguide (730). Waveguide (730) may further be included in a transmission assembly (not shown), such as transmission assembly (70) described above. For instance, waveguide (730) may be within an inner tubular actuating member and an outer sheath, with the sheath being coupled with rotating knob (720). In some versions, waveguide (730) may be decoupleable from lower handle portion (700). Examples of such decoupleable waveguides are described in U.S. patent application Ser. No. 13/269,870, entitled "Surgical Instrument with Modular Shaft and End Effector," filed Oct. 10, 2012, and published May 10, 2012 as U.S. Pat. Pub. No. 2012/0116388, now U.S. Pat. No. 9,510,895, issued Jan. 6, 2016, the disclosure of which is incorporated by reference herein.

Figure 17B:
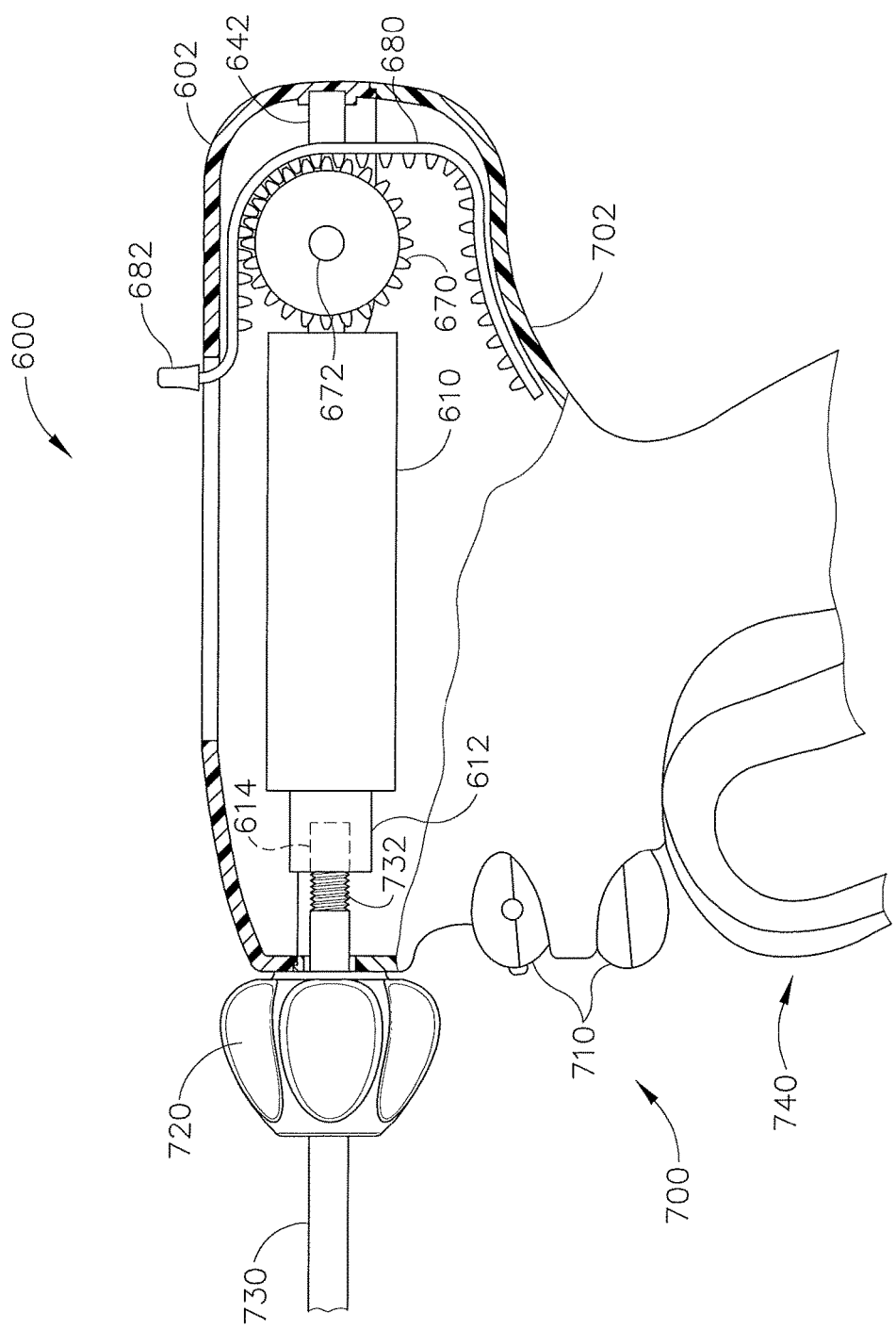
FIG. 17B depicts a side elevation view of the lower handle portion and transducer unit of FIG. 17A showing the transducer unit coupled to the lower handle portion.
Figure 17C:
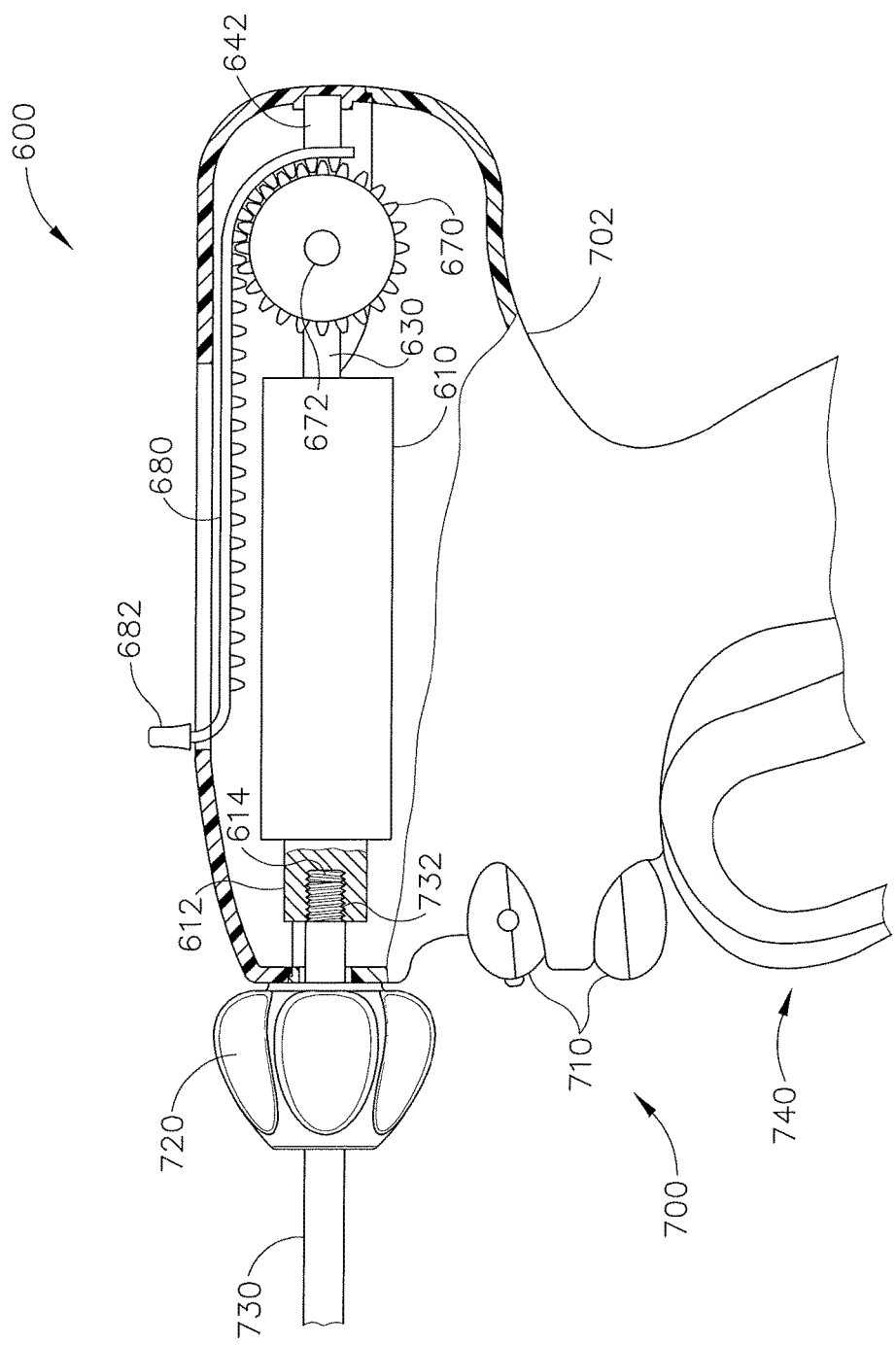
FIG. 17C depicts a side elevation view of the lower handle portion and transducer unit of FIG. 17A showing the rack gear actuated distally and the transducer coupled to the waveguide.

FIGS. 17A-17C depict a sequence showing the coupling of transducer (610) to waveguide (730) via a gear-driven coupling mechanism. FIG. 17A shows an initial configuration with transducer unit (600) and lower handle portion (700) decoupled and handle (682) of rack gear (680) shown in an uncoupled proximal position. Transducer unit (600) is subsequently lowered onto lower handle assembly (700) to align threading (732) of waveguide (730) with distal threaded recess (614) (shown in phantom) of transducer (610) as shown in FIG. 17B. In the present example, flexible rack gear (680) bends to fit within casing (702) of lower handle portion (700). In some versions, as discussed above, transducer unit (600) may be mechanically coupled to lower handle portion (700) via snap fasteners, clips, clamps, screws, bolts, interference fittings, latches, etc., though this is merely optional.

The user then actuates handle (682) distally along slot (606) of transducer unit (610). Handle (682), being coupled to rack gear (680), actuates rack gear (680) and engages the teeth of rack gear (680) with the teeth of pinion gear (670). Pinion gear (670) converts the linear motion of rack gear (680) into rotation. Since pinion gear (670) is fixedly coupled to main bevel gear (660), the rotation of pinion gear (670) also rotates main bevel gear (660). Main bevel gear (660) meshes with rear bevel gear (640) to rotate rear bevel gear (640). Support bevel gear (650), if included, may also rotate due to the rotation of rear bevel gear (640). Rear bevel gear (640) rotates transducer shaft (630), thereby threadably engaging distal threaded recess (614) of transducer (610) with threading (732) of waveguide (730). Waveguide (730) may then be slid proximally to torque into transducer (610). Of course, as noted above, in some versions transducer (610) may be slid distally such that distal threaded recess (614) engages threading (732) while waveguide (730) remains stationary. In some versions translation of handle (682) to the distal end of slot (606), as shown in FIG. 17C, may apply a predetermined number of rotations to transducer (610) to sufficiently torque transducer (610) to waveguide (730). By way of example only, transducer (610) may engage waveguide (730) for a predetermined number of rotations such that a torque of approximately 5 to 15 in-lbs. is formed. Of course other torque values may be used as well. In other versions, handle (682) may only need to be actuated partially along slot (606) to adequately torque transducer (610) onto waveguide (730). In such a version, various waveguides (730) and/or waveguides (730) with different threading (732) tolerances may be used with transducer unit (610) with little, if any, modification.

With transducer (610) coupled to waveguide (730), the user may then use the surgical instrument for a procedure. To decouple waveguide (730) from transducer (610), the user actuates handle (682) proximally, thereby engaging geared mechanism (620) to threadably disengage transducer (610) from waveguide (730). In addition or in the alternative, a second handle (not shown) may be coupled to the proximal end of rack gear (680) and extend through casing (702) and/or casing (602). Accordingly, the user may grasp this second handle and actuate the second handle upwardly and/or distally to engage geared mechanism (620) and threadably disengage transducer (610) from waveguide (730). As noted previously, a manual knob may be provided to initially break the torque connection between transducer (610) and waveguide (730). In some instances, the user may grasp rotation knob (720) to provide a counter torque when handle (682) is actuated proximally. Waveguide (730) and/or lower handle portion (700) may then be disposed of, cleaned, resterilized, and/or otherwise. Transducer unit (600) may be reused, cleaned, reclaimed, and/or otherwise as well. Thus, a user may dispose of the unclean mechanical components of waveguide (730) and/or lower handle portion (700) while recycling the electrical components of transducer unit (600). In some versions, a power unit may be within transducer unit (600) or within lower handle portion (700) for a portable surgical instrument. In other versions, transducer unit (600) may be coupled to a power source via a cable.

Of course other configurations for a gear-driven coupling mechanism will be apparent to one of ordinary skill in the art in view of the teachings herein. For instance, horn (612) and proximal end of waveguide (730) may be constructed in accordance with at least some of the teachings for waveguide assemblies (350, 380) and transducer assemblies (310, 370), shown in FIGS. 5-9. Alternatively, distal threaded recess (614) may omit the threading and waveguide (730) may omit threading (732). Proximal recess (616) may instead comprise threading and transducer shaft (630) may include threading complementary to the threading of proximal recess (616). In such a configuration, rotation of rear bevel gear (640) translates transducer (610) distally on the threading of transducer shaft (630), thereby compressively coupling transducer (610) to waveguide (730). The preceding configuration may be further modified such that horn (612) and proximal end of waveguide (730) may be constructed in accordance with at least some of the teachings for waveguide assembly (450) and transducer assembly (410), shown in FIG. 10. In other versions, a motor (not shown) may be operably coupled to geared mechanism (620). Still other versions will be apparent to one of ordinary skill in the art in view of the teachings herein.

IV. Exemplary Handle Assembly and Transducer Unit Slide Lock

In some instances it may be useful to selectively couple transducer unit (600) to lower handle portion (700). For instance, in some situations it may desirable to include the electrical components within a reusable transducer unit (600) while including only disposable mechanical components within lower handle portion (700). Such mechanical components may be rendered unclean during a procedure and may not be reusable. Accordingly, an exemplary slide lock assembly for coupling a transducer unit (600) to lower handle assembly (700) will be described below.

FIG. 18 shows an exemplary transducer unit (800) comprising a casing (810) and a slide lock assembly (820). It should be understood that a mirrored slide lock assembly (820) identical to the one shown in FIG. 18 may be included on the opposite side of transducer unit (800). Transducer unit (800) may be further configured in accordance with the teachings of transducer unit (700). Alternatively, transducer unit (800) may include a transducer (not shown) configured in accordance with one of the foregoing interfaces, as described in section II of the present disclosure. By way of example only, transducer unit (800) may include a transducer configured in accordance with the teachings for V-shaped slot interface (200) and configured to couple to a waveguide included in transmission assembly (880) of lower handle portion (850) described below.

Slide lock assembly (820) of the present example comprises a handle (822), a body member (824) (shown in phantom), and a pair of ledged sliders (826). In the present example, handle (822) extends out through a slot in the top of casing (810), though it should be understood that handle (822) may extend out a side, the front, or the rear of casing (810). In some versions slide lock assembly (820) may be adapted to be coupled to rack gear (680) and handle (682) such that actuation of handle (822) both locks transducer unit (800) to lower handle portion (850) and torques a transducer to a waveguide. In the present example, body member (824) couples handle (822) to the pair of ledged sliders (826). Ledged sliders (826) are L-shaped members each with a ledge (828) extending outwardly toward the side of casing (810). It should be understood that ledged sliders (826) may have other configurations, including slidable cylindrical pins, resilient clamp members configured to clamp onto cylindrical pins within lower handle portion (850), and/or any other configuration as will be apparent to one of ordinary skill in the art in view of the teachings herein.

Lower handle portion (850) of the present example comprises a casing (852), a pair of toggle buttons (860), a rotation knob (870), a transmission assembly (880), and a trigger (890) pivotally mounted to lower handle portion (850). Casing (852), toggle buttons (860), rotation knob (870), transmission assembly (880), and/or trigger (890) may be configured in accordance with at least some of the teachings of casing (61), the toggle buttons, rotation knob (66), transmission assembly (70), and/or trigger (68) described above or in accordance with U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660 (issued as U.S. Pat. No. 8,461,744); U.S. Pat. No. 6,500,176; U.S. Pat. Pub. No. 2011/0087218, now U.S. Pat. No. 8,939,974, issued Jan. 27, 2015; and/or U.S. Pat. Pub. No. 2009/0143797 (issued as U.S. Pat. No. 8,419,757). In the present example, casing (852) comprises a pair of slider recesses (854) formed in the inside of the side casing (852). It should be understood that a mirrored pair of slider recesses (854) identical to those shown in FIG. 18 may be included on the opposite side of casing (852). In the present example, each slider recess (854) comprises an entrance portion (856) and a ledge portion (858). Entrance portion (856) extends vertically out of casing (852) and has a longitudinal dimension sufficient to receive a ledged slider (826) therein. Ledge portion (858) of the present example extends proximally from entrance portion (856) and has a vertical dimension sized to receive the ledge (828) of ledged slider (826) therein. Ledge portion (858) may proximally extend from entrance portion for a distance less than, equal to, or more than the longitudinal length of ledge (828). Still other configurations for slider recesses (854) will be apparent to one of ordinary skill in the art in view of the teachings herein. For instance, ledge portions (858) of slider recesses (854) may be ramped downwardly to urge ledges (828) downwardly, thereby further tightening transducer unit (800) to lower handle portion (850). In another arrangement, slider recesses (854) may omit entrance portion (856) and only include the ramped ledge portions (858) previously described.

When a user desires to couple transducer unit (800) to lower handle portion (850), initially ledged sliders (826) are aligned with entrance portions (856). Transducer unit (800) is then lowered onto lower handle portion (850) such that ledges (828) are longitudinally aligned with ledge portions (858). The user then actuates handle (822) proximally to slide ledges (828) of ledged sliders (826) into ledge portions (858), thereby coupling transducer unit (800) to lower handle portion (850). The user may then use the assembled surgical instrument for a procedure. When a user desires to decouple transducer unit (800) from lower handle portion (850), the user actuates handle (822) distally until ledges (828) are vertically clear of ledge portions (858). The user may then lift transducer unit (800) off of lower handle portion (850). Lower handle portion (850) may then be disposed of, cleaned, resterilized, and/or otherwise. Transducer unit (800) may be reused, cleaned, reclaimed, and/or otherwise as well. Thus, a user may dispose of the unclean mechanical components of lower handle portion (850) while recycling or reusing the components of transducer unit (800). In some versions, a power unit may be within transducer unit (800) for a portable surgical instrument. In other versions, transducer unit (800) may be coupled to a power source via a cable.

Of course other configurations for a slide lock assembly will be apparent to one of ordinary skill in the art in view of the teachings herein. For instance, slider recesses (854) may include one or more detents to selectively hold slide lock assembly (820) in the proximal position.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body portion comprising:
      (i) a body casing, and
      (ii) a waveguide extending distally from the body casing; and
   (b) a transducer unit comprising:
      (i) a transducer, and
      (ii) a geared assembly configured to selectively couple the transducer to the waveguide by rotating and translating the transducer relative to the waveguide.

2. The surgical instrument of claim 1 wherein the geared assembly comprises a plurality of bevel gears and a shaft, wherein the shaft is coupled to the transducer and coupled to at least one of the plurality of bevel gears.

3. The surgical instrument of claim 2 wherein at least one bevel gear of the plurality of bevel gears is coupled to a pinion gear.

4. The surgical instrument of claim 3 further comprising a rack gear, wherein the pinion gear engages the rack gear, wherein the rack gear is translatable relative to the pinion gear.

5. The surgical instrument of claim 4 wherein the rack gear is flexible.

6. The surgical instrument of claim 4 wherein the rack gear is rigid.

7. The surgical instrument of claim 4, wherein the transducer unit further comprises a transducer casing, the instrument further comprising a handle coupled to a distal end of the rack gear and a slot formed in the transducer casing, wherein a portion of the handle extends through the slot, and wherein the handle is translatable relative to the slot.

8. The surgical instrument of claim 2 wherein the shaft comprises threading, wherein the transducer comprises a proximal threaded recess complementary to the threading of the shaft, and wherein the shaft is operable to translate the transducer relative to the shaft.

9. The surgical instrument of claim 8 wherein the transducer is selectively coupleable to the waveguide by an interference fitting.

10. The surgical instrument of claim 2 wherein the waveguide comprises threading formed on a proximal end of the waveguide, wherein the transducer comprises a horn having a threaded recess complementary to the threading of the waveguide, wherein the shaft is fixedly coupled to the transducer, and wherein the shaft is operable to thread the threading of the waveguide into the threaded recess of the transducer.

11. The surgical instrument of claim 2, wherein the transducer unit further comprises a transducer casing, wherein the shaft is fixedly coupled to the transducer, and wherein the shaft is operable to rotate the transducer relative to the transducer casing.

12. The surgical instrument of claim 11 wherein the waveguide comprises a male connector at a proximal end of the waveguide, wherein the transducer comprises a female recess formed in a distal end and configured to receive the male connector, and wherein the shaft is operable to rotate the transducer having the female recess about the male connector to selectively couple the transducer to the waveguide.

13. The surgical instrument of claim 11 wherein the waveguide comprises an elliptic cylinder projection at a proximal end, wherein the transducer comprises an ovular recess formed in a distal end and configured to receive the elliptic cylinder projection, and wherein the shaft is operable to rotate the transducer when the elliptic cylinder is within ovular recess.

14. The surgical instrument of claim 1 wherein the transducer unit is coupleable to the body portion.

15. The surgical instrument of claim 1 wherein the transducer unit comprises a slide lock assembly, wherein the lower body portion comprises a slider recess formed in the body casing, and wherein the slide lock assembly is operable to selectively couple the transducer unit to the lower body portion via insertion into the slider recess.

16. A surgical instrument comprising:
   (a) a body portion comprising:
      (i) a body casing, and
      (ii) a waveguide extending distally from the body casing; and
   (b) a transducer unit comprising:
      (i) a transducer, and
      (ii) at least one gear configured to selectively couple the transducer to the waveguide by rotating and translating the transducer relative to the waveguide and relative to the body casing.

17. A surgical instrument comprising:
   (a) a body portion comprising:
      (i) a body casing, and
      (ii) a waveguide extending distally from the body casing; and
   (b) a transducer unit comprising:
      (i) a transducer, and
      (ii) one or more gears configured to selectively drive the transducer into engagement with the waveguide by rotating and translating the transducer relative to the body casing.

* * * * *